US008163481B2

(12) United States Patent
Rodriguez-Collazo et al.

(10) Patent No.: US 8,163,481 B2
(45) Date of Patent: Apr. 24, 2012

(54) METHOD OF EXTRACTING CHROMATIN FRACTIONS FROM INTACT CELLS

(75) Inventors: Pedro Rodriguez-Collazo, Pittsburgh, PA (US); Sanford Harrison Leuba, Pittsburgh, PA (US); Jordanka Zlatanova, Laramie, WY (US)

(73) Assignees: University of Pittsburgh - of the Commonwealth Systems of Higher Education, Pittsburgh, PA (US); University of Wyoming, Laramie, WY (US)

( * ) Notice: Subject to any disclaimer, the term of this patent is extended or adjusted under 35 U.S.C. 154(b) by 599 days.

(21) Appl. No.: 12/061,234

(22) Filed: Apr. 2, 2008

(65) Prior Publication Data

US 2008/0241845 A1  Oct. 2, 2008

Related U.S. Application Data

(60) Provisional application No. 60/909,491, filed on Apr. 2, 2007.

(51) Int. Cl.
 *C12Q 1/68* (2006.01)
(52) U.S. Cl. ...................................................... 435/6.1
(58) Field of Classification Search ........................ None
 See application file for complete search history.

(56) References Cited

U.S. PATENT DOCUMENTS 6,953,687 B1 * 10/2005 Rybak et al. ............... 435/320.1

OTHER PUBLICATIONS

Chen-Cleland et al. (J Biol Chem. Nov. 5, 1993;268(31):23409-16).*
Acharya MR, Sparreboom A, Venitz J, Figg WD.Rational development of histone deacetylase inhibitors as anticancer agents: a review. Mol Pharmacol. Oct. 2005;68(4):917-32. Epub Jun. 14, 2005.
Anest V, Hanson JL, Cogswell PC, Steinbrecher KA, Strahl BD, Baldwin AS. A nucleosomal function for IkappaB kinase-alpha in NF-kappaB-dependent gene expression. Nature. Jun. 5, 2003;423(6940):659-63.
Ansevin AT, Hnilica LS, Spelsberg TC, Kehm SL. Structure studies on chromatin and nucleohistones. Thermal denaturation profiles recorded in the presence of urea. Biochemistry. Dec. 7, 1971;10(25):4793-803.
Bloom KS, Anderson JN. Fractionation and characterization of chromosomal proteins by the hydroxyapatite dissociation method. J Biol Chem. Jun. 25, 1978;253(12):4446-50.
Blüthmann H, Mrozek S, Gierer A. Non-histone chromosomal proteins. Their isolation and role in determining specificity of transcription in vitro. Eur J Biochem. Oct. 15, 1975;58(2):315-26.
Bolund LA, Johns EW. The selective extraction of histone fractions from deoxyribonucleoprotein. Eur J Biochem. Jun. 15, 1973;35(3):546-53.
Brocklehurst K, Carlsson J, Kierstan MP, Crook EM. Covalent chromatography. Preparation of fully active papain from dried papaya latex. Biochem J. Jul. 1973;133(3):573-84.
Brownell JE, Zhou J, Ranalli T, Kobayashi R, Edmondson DG, Roth SY, Allis CD. Tetrahymena histone acetyltransferase A: a homolog to yeast Gcn5p linking histone acetylation to gene activation. Cell. Mar. 22, 1996;84 (6):843-51.
Choi HS, Choi BY, Cho YY, Mizuno H, Kang BS, Bode AM, Dong Z. Phosphorylation of histone H3 at serine 10 is indispensable for neoplastic cell transformation. Cancer Res. Jul. 1, 2005;65(13):5818-27.
Dunn KL, Davie JR. Stimulation of the Ras-MAPK pathway leads to independent phosphorylation of histone H3 on serine 10 and 28. Oncogene. May 12, 2005;24(21):3492-502.
Espino PS, Drobic B, Dunn KL, Davie JR. Histone modifications as a platform for cancer therapy. J Cell Biochem. Apr. 15, 2005;94(6):1088-102.
Felsenfeld G, Groudine M. Controlling the double helix. Nature. Jan. 23, 2003;421(6921):448-53.
Galasinski SC, Resing KA, Ahn NG. Protein mass analysis of histones. Methods. Sep. 2003;31(1):3-11.
Galasinski SC, Resing KA, Ahn NG. Protein mass analysis of histones. Methods. Sep. 2003;31(1):3-11. Garcia BA, Barber CM, Hake SB, Ptak C, Turner FB, Busby SA, Shabanowitz J, Moran RG, Allis CD, Hunt DF. Modifications of human histone H3 variants during mitosis. Biochemistry. Oct. 4, 2005;44(39):13202-13.
Gehringer MM. Microcystin-LR and okadaic acid-induced cellular effects: a dualistic response. FEBS Lett. Jan. 16, 2004;557(1-3):1-8.
Iizuka M, Smith MM. Functional consequences of histone modifications. Curr Opin Genet Dev. Apr. 2003;13(2):154-60.
Janssens V, Goris J, Van Hoof C. PP2A: the expected tumor suppressor. Curr Opin Genet Dev. Feb. 2005;15(1):34-41.
Jencks, William P. Catalysis in Chemistry and Enzymology. Dover Publications, 1987: pp. 358-436.
Johns EW, Forrester S, Riches PL. A method for the large-scale preparation of the two halves of histone fraction F2B. Arch Biochem Biophys. Sep. 1972;152(1):287-90.
Johns EW. A method for the selective extraction of histone fractions f2(a)1 and f2(a)2 from calf thymus deoxyribonucleoprotein at pH7. Biochem J. Nov. 1967;105(2):611-4.
Lorch Y, Kornberg RD. Isolation of the yeast histone octamer. Proc Natl Acad Sci U S A. Nov. 8, 1994;91(23):11032-4.
Mahadevan LC, Willis AC, Barratt MJ. Rapid histone H3 phosphorylation in response to growth factors, phorbol esters, okadaic acid, and protein synthesis inhibitors. Cell. May 31, 1991;65(5):775-83.
Nowak SJ, Corces VG. Phosphorylation of histone H3: a balancing act between chromosome condensation and transcriptional activation. Trends Genet. Apr. 2004;20(4):214-20.
Rickwood D, MacGillivray AJ. Improved techniques for the fractionation of non-histone proteins of chromatin on hydroxyapatite. Eur J Biochem. Feb. 21, 1975;51(2):593-601.
Rodriguez P, Ruiz MT, Price GB, Zannis-Hadjopoulos M. NAP-2 is part of multi-protein complexes in HeLa cells. J Cell Biochem. Oct. 1, 2004;93(2):398-408.

(Continued)

*Primary Examiner* — Christopher M Babic
(74) *Attorney, Agent, or Firm* — The Webb Law Firm

(57) ABSTRACT

Methods are provided for isolation of chromatin fractions of nucleoproteins containing histone H1, H2A, H2B, H3 and H4 proteins and/or histone H1, H2A, H2B, H3 and/or H4 proteins, from intact cells. The methods preserve original patterns of covalent modifications of the histone proteins.

74 Claims, 12 Drawing Sheets

OTHER PUBLICATIONS

Rodriguez P, Fuentes D, Munoz E, Rivero D, Orta D, Alburquerque S. The streptokinase domain responsible for plasminogen binding. Fibrinolysis, 1994, 8 (5), pp. 276-285.

Rogakou EP, Redon C, Boon C, Johnson K, Bonner WM. Rapid histone extraction for electrophoretic analysis. Biotechniques. Jan. 2000;28(1):38-40, 42, 46.

Sassone-Corsi P, Mizzen CA, Cheung P, Crosio C, Monaco L, Jacquot S, Hanauer A, Allis CD. Requirement of Rsk-2 for epidermal growth factor-activated phosphorylation of histone H3. Science. Aug. 6, 1999;285(5429):886-91.

Schönthal AH. Role of serine/threonine protein phosphatase 2A in cancer. Cancer Lett. Sep. 10, 2001;170(1):1-13.

Sivaraman VS, Wang H, Nuovo GJ, Malbon CC. Hyperexpression of mitogen-activated protein kinase in human breast cancer. J Clin Invest. Apr. 1, 1997;99(7):1478-83.

Spelsberg TC, Hnilica LS. Proteins of chromatin in template restriction. I. RNA synthesis in vitro. Biochim Biophys Acta. Jan. 1, 1971;228(1):202-11.

Spelsberg TC, Hnilica LS. Proteins of chromatin in template restriction. II. Specificity of RNA synthesis. Biochim Biophys Acta. Jan. 1, 1971;228(1):212-22.

Spelsberg TC, Hnilica LS, Ansevin AT. Proteins of chromatin in template restriction. 3. The macromolecules in specific restriction of the chromatin DNA. Biochim Biophys Acta. Jan. 28, 1971;228(2):550-62.

Strahl BD, Allis CD. The language of covalent histone modifications. Nature. Jan. 6, 2000;403(6765):41-5.

Taunton J, Hassig CA, Schreiber SL. A mammalian histone deacetylase related to the yeast transcriptional regulator Rpd3p. Science. Apr. 19, 1996;272(5260):408-11.

Taverna SD, Ueberheide BM, Liu Y, Tackett AJ, Diaz RL, Shabanowitz J, Chait BT, Hunt DF, Allis CD. Long-distance combinatorial linkage between methylation and acetylation on histone H3 N termini. Proc Natl Acad Sci U S A. Feb. 13, 2007;104(7):2086-91.

* cited by examiner

METHOD OF EXTRACTING CHROMATIN FRACTIONS FROM INTACT CELLS

CROSS REFERENCE TO RELATED APPLICATIONS

This application claims the benefit under 35 U.S.C. §119 (e) to U.S. Provisional Patent Application No. 60/909,491, filed on Apr. 2, 2007, which is incorporated herein by reference in its entirety.

STATEMENT REGARDING FEDERAL FUNDING

This invention was made with government support under Grant No. CA122177 awarded by the National Cancer Institute. The government has certain rights in the invention.

A method is provided for simple and inexpensive extraction of chromatin fractions from intact cells. The chromatin fractions include nucleoproteins comprising H3 and H4 histone proteins as well as isolated, functional H1, H3 and/or H4 histone proteins that retain their original covalent modifications.

Histone H3 and H4 are important structural and functional pillars of the chromatin. Their post-translational covalent modifications are involved in basic DNA-template processes, such as transcriptional activation, DNA replication, repair, recombination and segregation. Deregulation of H3 and H4 modifications may be involved in the etiology of a variety of human diseases. Therefore, implementation of a simple and reliable method for analysis of in vivo H3 and H4 covalent modification is pivotal.

Since 1996, with the discovery that Gcn5, a transcriptional co-activator in yeast possessing histone acetyltransferase activity (Brownell, J. E. et al. Tetrahymena histone acetyltransferase A: a homolog to yeast Gcn5p linking histone acetylation to gene activation. Cell 84, 843-851 (1996)); and the identification of the first histone deacetylase (Taunton, J., Hassig, C. A. & Schreiber, S. L. A mammalian histone deacetylases related to the yeast transcriptional regulator Rpd3p. Science 272, 408-411 (1996), a number of histone modifications have been connected to multiple DNA-template processes. As a consequence, in recent years, the notion has emerged that deregulation of covalent histone biomarkers may lead to a variety of diseases, such as cancer development (see, e.g., Histone Modifications as a Platform for Cancer Therapy Paula S. Espino, Bojan Drobic, Katherine L. Dunn, and James R. Davie Journal of Cellular Biochemistry 94: 1088-1102 (2005) and Functional consequences of histone modifications Masayoshi Iizuka and M Mitchell Smith Current Opinion in Genetics & Development 2003, 13:154-160).

Increasing evidence has placed covalent post-translational modifications of histones H3 and H4 centrally in controlling DNA template processes (Felsenfeld, G. et al. (2003) Controlling the double helix. Nature 421, 448-453 and Strahl, B. D. et al. (2000) The language of covalent histone modification. Nature 403, 41-45). Dynamic analysis of the fluctuations of histone modifications in response to environmental changes can be achieved by using specific antibodies against modified amino acid residues on each histone in immunoblotting assays. Although this technique has been proven to be useful, epitope occlusion by modifications close to the targeted amino acid has been documented. Moreover, collecting global information on changes in bulk histone modifications during cell cycle progression or in response to changes in environment, using modification-specific antibodies is an unrealistic task. In the best scenario, the antibodies can offer a relative, semi-quantitative value for a particular modified residue. Absolute values for specific modifications can be obtained through measurements of the absolute protein mass (Galasinski S C et al. (2003) Protein mass analysis of histones. Methods. 31(1): 3-11) or by measuring the radioactive decay of in vivo isotopically labeled residues (e.g. phosphorylation and acetylation). Moreover, proteomic analysis of fast and dynamically fluctuating H3/H4 modifications, for large number of samples, is limited by the availability of H3/H4.

Most of the techniques to obtain histones in large quantities require cell lysis, nuclei purification, chromatin solubilization and histone isolation by a variety of chromatographic techniques (Garcia, B. A. et al., Modifications of Human Histone H3 Variants during Mitosis, Biochemistry 2005, 44, 13202-13213; Taverna, S. D. et al., Long-distance combinatorial linkage between methylation and acetylation on histone H3 N termini (2002) Cell 110: 701-711; Johns E W et al. (1972). A method for the large-scale preparation of the two halves of histone fraction F2B. Arch Biochem Biophys. September; 152(1): 287-90; Johns E. W. A method for the selective extraction of histone fractions f2(a) 1 and f2(a)2 from calf thymus deoxyribonucleoprotein at pH7. Biochem J. 1967 November; 105(2): 611-4; Bloom K S et al. Fractionation and characterization of chromosomal proteins by the hydroxyapatite dissociation method. J Biol Chem. 1978 Jun. 25; 253 (12): 4446-50; Bluthmann H et al. Non-histone chromosomal proteins. Their isolation and role in determining specificity of transcription in vitro. Eur J Biochem. 1975 Oct. 15; 58(2): 315-26; Rickwood D, MacGillivray A J. Improved techniques for the fractionation of nonhistone proteins of chromatin on hydroxyapatite. Eur J Biochem. 1975 Feb. 21; 51(2): 593-601; Bolund L A, Johns E W. The selective extraction of histone fractions from deoxyribonucleoprotein. Eur J Biochem. 1973 Jun. 15; 35(3): 546-53; Rogakou E P, Redon C, Boon C, Johnson K, Bonner W M. Rapid histone extraction for electrophoretic analysis. Biotechniques. 2000 January; 28(1): 38-40, 42, 46; and Lorch Y, Kornberg R D. Isolation of the yeast histone octaves. Proc Natl Acad Sci U S A. 1994 Nov. 8; 91(23): 11032-4). These various steps may lead to artefactual histone modifications that do not necessarily reflect the in vivo H3/H4 modification patterns. It is therefore desirable to have an inexpensive, simple method for isolating histone proteins that does not interfere with histone modifications, that is suitable for both clinical and basic research use, and which prevents alteration of histone modifications by enzymatic activity.

SUMMARY

Methods are described herein for isolating chromatin fractions, for example a nucleoprotein fraction containing H1, H3 and H4 histone proteins (an H1/H3/H4/DNA chromatin fraction), a fraction containing isolated H3 and H4 histone proteins, isolated H3 histone protein, isolated H4 histone protein, isolated H2A and H2B histone protein, core histone proteins or isolated H1 histone protein. The chromatin fractions are obtained from intact cells and preserve the original histone covalent modification patterns.

In one embodiment, the method relies on stabilization of the nuclei and chromatin in solutions of a chaotropic reagent (e.g., a denaturing reagent) and a salt at particular concentrations, for example and without limitation a solution of 8 M (8 molar) to 10 M urea, also a salt, such as an inorganic salt or a fully ionized salt. The cell cytoplasm and chromatin proteins other than H3, H4 and H1 are solubilized, while the H3/H4 tetramer, and to some extent H1 remains chromatin-associated. This allows for collection of the chromatin by centrifugation at 14K for about 5-10 minutes (e.g., in a typical microcentrifuge). Uncontrolled enzymatic activities that may lead to perturbation of the in vivo H3/H4 modifications or to proteolysis instigated by cell lysis are instantaneously stopped by the presence of high concentrations of the chaotropic reagent, such as a high urea concentration. The dissociation of highly phosphorylated H2A and low molecular mass polypeptides from the chromatin by the methods described herein, allows for direct analysis of $^{32}$P-metabolically labeled histones H3/H4 by SDS-PAGE or determination of histone H3/H4 phosporylation or post-translational modification by immunoblot analysis, avoiding the use of costly and complicated techniques such RP-HPLC as a preliminary step for histone isolation. The methods described herein produce functional, isolated H3 and/or H4 proteins.

In one embodiment, a method of isolating a chromatin fraction containing histone H1, H3 and H4 proteins from an intact cell is provided. The method comprises lysing cells in a first solution comprising an enzyme-inhibitory concentration of a chaotropic reagent to produce a lysate, wherein either: the first solution comprises a fully ionic salt; or an a fully ionic salt is added to the lysate, wherein the fully ionic salt is included in the first solution or is added to the lysate in an amount effective, in the lysate, to prevent chromatin expansion and to facilitate dissociation, inactivation and extraction of cellular components other than H3, H4 and H1 from the chromatin. In a further embodiment, the method further comprises washing the released chromatin in a second solution comprising an enzyme-inhibitory concentration of a chaotropic reagent and an amount of a fully ionic salt effective to facilitate dissociation, inactivation and extraction of cellular components other than H3, H4 and H1 from the chromatin in the solution. The chaotropic reagent may be, without limitation, one of urea, thiourea, guanidium isothiocyanate, guanidium HCl, ammonium isothiocyanate and LiI. In one non-limiting embodiment, the chaotropic reagent in one or both of the first and second solution is urea. The salt may comprise, without limitation, one or more of the following ions: Mg, Ca, Na, K, Li, $NH_4$, $SO_4$, acetate, Cl, F, Br, I, phosphate, bicarbonate and borate. In one non-limiting embodiment, the salt is NaCl.

The chromatin fraction is, for example and without limitation: chromatin containing predominantly H1, H3 and H4 histone proteins; a mixture of H1, H3 and H4 histone proteins; a mixture of isolated H3 and H4 histone proteins; and isolated H1, H3 or H4 histone proteins.

The method may further comprise extracting H1, H3 and H4 histone proteins from the DNA, for example and without limitation, as described below. H1 protein may be separated from the H3/H4 proteins by differential precipitation in perchloric acid. The H3 histone protein may be separated from the H4 histone protein by any method, for example and without limitation by affinity chromatography or by binding the free SH— group of the H3 protein to a support.

In a further non-limiting embodiment, the lysate is adsorbed to a non-sequence-specific DNA adsorbing material, such as, without limitation hydroxyapatite. This can facilitate handling of the chromatin material.

According to another embodiment, a method of separating histone H3 protein from histone H4 protein in a sample comprising histone H3 and H4 proteins is provided. The method comprises binding histone H3 protein to a sulfhydryl-reactive group attached to a surface and washing histone H4 from the surface. The method may further comprise eluting histone H3 from the surface with a reducing agent after washing histone H4 from the surface. The surface may be a bead, such as an agarose bead, for example Sepharose. The sulfhydryl-reactive group may be chosen from one or more of maleimide; haloacetyl; pyridyl disulfide; pyridyl-thiopropyl; pyridyl-glutathion; N-succinimidyl-6-(3'-(2-pyridyldithio)-propionamido)-hexanoate; N-succinimidyl-3-(2-pyridyldithio)-propionate; sulfosuccinimidyl-6-(3'-(2-pyridyldithio)-propionamido)-hexanoate); activated thiol; thiopropy; 3-(2-pyridyldithio)propionyl hydrazide; 4-succinimidyloxycarbonyl-methyl-a-[2-pyridyldithio]toluene; and 1-methylpropyl 2-imidazoylyl disulfide. In certain non-limiting embodiments the sulfhydryl-reactive group is one or both of pyridyl-thiopropyl and pyridyl-gluthation.

According to yet another embodiment, a method of isolating histone proteins from cells is provided which comprises lysing the cells in an acid to produce a lysate, neutralizing the acid, binding the lysate to a cationic exchange material at a salt concentration at which histone proteins bind to the cationic exchange material, washing the cationic exchange material to remove non-histone proteins (and H1 and, optionally H2A/H2B histone proteins), eluting one or more histone proteins with elution solutions having a salt concentration sufficiently high to elute the one or more histone proteins. As with the chaotropic agent described above, the acid treatment serves to preserve the histone modification patterns. The acid may be any acid useful for the purpose, for example and without limitation $H_2SO_4$, typically in the range of 0.1M to 0.25 M, and for example and without limitation, 0.1 or 0.2 M.

The cationic exchange material typically is a cationic exchange resin. In one non-limiting embodiment, the cationic exchange material is a sulfopropyl agarose, such as SP-Sepharose, as described below. The salt typically, but not exclusively is NaCl. The method comprises eluting histone proteins from the cationic exchange material with amounts of salt, such as, without limitation, NaCl. The concentration of the salt used in the elution solution determines which histone fraction is eluted. Typically the lysate is bound to the cationic exchange material at a lower ionic concentration, at which all histone binds to the material, for example and without limitation, 0.1 to 0.5 M NaCl, or 0.2 M NaCl. The cationic exchange material can be washed with a salt solution effective to remove most non-histone proteins, but not to elute a desired histone fraction, such as histone H1, which, of the histone proteins, elutes at the lowest salt concentration, for example and without limitation with 0.6 M NaCl. Once washed, H1 histone can be eluted with an elution solution having a salt concentration effective to elute histone H1 protein, but essentially not other histone proteins (in other words, the salt concentration is high enough to elute H1, but the predominance of other histone proteins remain bound to the cationic exchange material). Histone H1 may be eluted with 0.6 M NaCl.

Once histone H1 is eluted, or even before it is eluted, core histones or core histones plus H1 (if H1 is not previously eluted) can be eluted from the cationic exchange material with an elution solution having a salt concentration effective to elute the core histones from the cationic exchange material. For example and without limitation NaCl concentrations of 1M or above, for example and without limitation, 2M NaCl, can be used for this purpose. To selectively elute histone H2A and H2B proteins, a (first) elution solution having a salt concentration effective to elute histone H2A and H2B proteins, but essentially not histone H3 or H4 histone proteins can be utilized. The (first) elution solution may comprise NaCl in a concentration ranging from 0.7 M to 1 M, for example and without limitation 0.8 M NaCl. Optionally, after eluting the histone H2A and H2B proteins, histone H3 and H4 proteins can be eluted with a second elution solution having a salt concentration effective to elute histone H3 and H4 proteins, such as 2 M NaCl.

Provided in another embodiment is a composition comprising a histone chromatin fraction prepared according to the method described above and/or herein. As above, the chromatin fraction is, for example and without limitation: chromatin containing predominantly H1, H3 and H4 histone proteins; a mixture of H1, H3 and H4 histone proteins; a mixture of isolated H3 and H4 histone proteins; and isolated H1, H3 or H4 histone proteins.

Also provided is a kit comprising a container containing a solution comprising a chaotropic agent and a salt each in an amount effective to lyse cells according to a method described herein and an indicia providing instructions relating to one or more of isolation of a chromatin fraction containing H1, H3 and H4 histone proteins using the solution and isolation of one or more of H1, H3 and H4 histone proteins using the solution. The kit may further comprise one or more of a wash solution comprising a chaotropic agent and a salt; a surface comprising one or more of a binding agent specific to H3 histone, a binding agent specific to H4 histone, and a sulfhydryl-reactive group; a non-sequence-specific DNA adsorbing material and a centrifuge filter.

In yet another embodiment, a method is provided of evaluating chromatin structure or histone modification patterns in a biological sample, such as a biopsy or cell culture, comprising, evaluating one or more of post-translational modification patterns, DNA binding patterns and chromatin assembly function of a chromatin fraction prepared in the manner described above. In a non-limiting embodiment, the chromatin fraction may be evaluated for one or more of the following post-translational modifications: phosphorylation, acetylation, methylation, ubiquitination, sumoylation, poly-ribosylation, poly-polyglutamylation, nitrosylation and sulfatation. The chromatin fraction also may be evaluated for chromatin assembly function by determining, for example and without limitation, the ability of proteins of the chromatin fraction to supercoil DNA in a DNA supercoiling assay.

DETAILED DESCRIPTION

Figure 1:
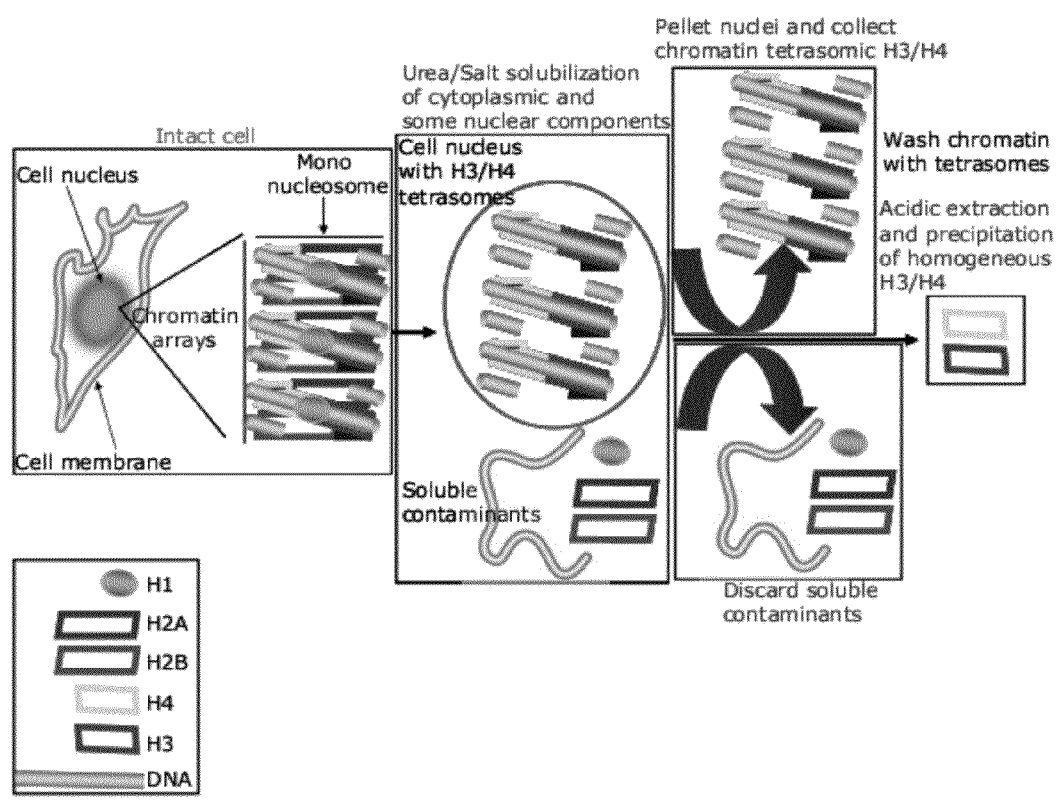
FIG. 1 is an illustrative cartoon of a H3/H4 histone protein extraction from intact cells according to one embodiment of the present invention.

Methods are provided herein for isolating chromatin fractions from intact cells. The chromatin fractions include histone H2A, H2B, H3, H4 and H1 histone proteins, associated with DNA or in isolated form. The methods preserve histone covalent modifications, for example and without limitation phosphorylation state. The methods are inexpensive and simple and can be performed by untrained individuals with only a minimum of training. The methods also may be partially or fully automated.

In a first embodiment, a method is provided comprising contacting intact cells with an aqueous solution comprising a chaotropic reagent and a salt effective for the stated purpose, which, when combined, leads to solubilization and extraction of most cellular proteins, with the exception of H3, H4 and, to some extent, H1 histone proteins. According to another embodiment, intact cells are lysed in acid and adsorbed to a cationic exchange material which permits washing to remove non-histone cellular components, and selective elution with salt of various histone fractions. In yet another embodiment, H3 and H4 histone proteins can be separated by binding a composition comprising both proteins to a sulfhydryl-reactive group-containing surface or substrate, washing H4 (unbound) histone from the surface or substrate and optionally eluting H3 histone from the surface with an elution solution comprising a reducing agent.

In the first embodiment, in which a chaotropic agent is used to lyse cells (and in other methods/steps described herein in which a chaotropic agent is utilized), the chaotropic agent is used in concentrations sufficient to halt or substantially halt enzymatic processes and/or to denature protein to a desired extent. By "chaotropic reagent" it is meant a reagent that disrupts protein function by unfolding its three-dimensional structure, yet does not destroy the primary amino acid structure sequence of a protein. The chaotropic reagent may be, for example and without limitation: urea, thiourea, guanidium isothiocyanate (guanidium SCN), guanidium HCl or LiI. In the case of urea, in order to halt enzymatic activity, concentrations in the range from 8 M to 10 M may be used, including, without limitation 8 M, 9 M and 10 M and increments therebetween or functionally equivalent concentrations on or about that range. In the case of guanidium, in order to halt enzymatic activity, the concentration typically is at least about 6M.

Salts useful in the various methods described herein include, without limitation a salt comprising one or more of the following ions: Mg, Ca, Na, K, Li, $NH_4$, $SO_4$, acetate, Cl, F, Br, I, phosphate, bicarbonate and borate (charge omitted).

These salts can be described as fully ionic in that, in an aqueous solution they typically are fully, substantially or essentially dissociated into their respective ionic constituents. One non-limiting example of a useful, fully ionic salt is NaCl.

In the first embodiment in which a chaotropic agent is used to lyse cells, the salt is used in a quantity effective to prevent chromatin expansion and to allow protein extraction. Chromatin expansion typically is present when the chaotropic reagent is used by itself. For purposes of stabilizing cellular components, e.g. in a lysis or a chromosome, chromatin and/or nucleus wash solution described herein, NaCl may be employed in a range of between about 10 mM and about 1M and any effective increment there between, for instance and without limitation, 10 mM, 25 mM, 50 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 900 mM and 1000 mM. Other non-limiting examples of useful salts include: NaCl, KCl, $MgCl_2$, $CaCl_2$, $Na_3SO_4$, $Mg_3(SO_4)_2$, $Ca_3(SO_4)_2$, $Mg_3(PO_4)_2$, and $Ca_3(PO_4)_2$.

In one non-limiting embodiment, the method comprises incubating logarithmically growing mammalian cells in 8 M urea, 20 mM Tris-HCl pH 8 and in concentrations of NaCl ranging from about 10 mM to about 800 mM, resulting in extraction of cytoplasmic and most nuclear proteins (among them H2A/H2B), other than H3, H4 and, to some extent, H1 histone proteins. The added salt, without limitation, is believed to stabilize the nuclear envelope by inducing and stabilizing hydrophobic interactions that hold together the nuclear envelope, whereas the cell cytoplasm and other nuclear components are solubilized and washed off, while H3-H4 can be recovered by conventional microcentrifugation of extracted nuclei. This permits collection of, as well as separation from contaminating biopolymers, the nuclei and chromatin structures containing the majority of H3 and H4 using low-speed centrifugation. In other embodiments, prior to lysis, the cells may be purposefully arrested at any growth stage, synchronized in their cell cycles according to known methods, or treated with any compound(s) or composition(s).

The methods described herein for chromatin fractionation can result in highly purified H3/H4 protein, which can be obtained from a variety of cell lines or from tissue samples in a simple manner with high yield. The method bypasses common steps of nuclei isolation, chromatin DNA digestion and any chromatographic or gradient-ultra centrifugation of the samples.

The methods described herein are useful in both biomedical research and in clinical investigation and diagnosis. Histone modifications, including, without limitation, phosphorylation, acetylation, methylation, ubiquitination, sumoylation, poly-ribosylation poly-glutamylation, nitrosylation and sulfatation are involved in most cellular process, since those modification control gene expression and other nuclear processes, and altered histone modification patterns are implicated in a number of diseases. See, generally: Mahadevan, L.C. et al. (1991) Rapid histone H3 phosphorylation in response to growth factors, phorbol esters, okadaic acid, and protein synthesis inhibitors. Cell 65, 775-783; Dunn, K. L. et al. (2005) Stimulation of the Ras-MAPK pathway leads to independent phosphorylation of histone H3 on serine 10 and 28. Oncogene 24, 3492-3502; Sivaraman, V. S. et al. (1997) Hyperexpression of mitogen-activated protein kinase in human breast cancer. J Clin Invest 99, 1478-1483; Gehringer, M. M. (2004) Microcystin-LR and okadaic acid-induced cellular effects: a dualistic response. FEBS Lett 557, 1-8; Schonthal, A. H. (2001) Role of serine/threonine protein phosphatase 2A in cancer. Cancer Lett 170, 1-13; Nowak, S. J. et al. (2004) Phosphorylation of histone H3: a balancing act between chromosome condensation and transcriptional activation. Trends Genet 20, 214-20; and Anest, V. et al. (2003) A nucleosomal function for IkappaB kinase-alpha in NF-kappaB-dependent gene expression. Nature 423, 659-63. For example, and without limitation, Sassone-Corsi P. et al. Requirement of Rsk-2 for epidermal growth factor-activated phosphorylation of histone H3 Science 1999 Aug. 6; 285 (5429): 886-91, showing how a mutation of an enzyme (Rsk2) from the MAPK pathway, which is responsible for serine 10 phosphorylation on H3, leading to mental retardation among other clinical manifestations.

For biomedical research, the methods can be used for investigation of in vivo chromatin structure and dynamics, for example and without limitation, how histone modifications fluctuate in response to environmental changes. The methods would assist in unveiling the role of histone modifications in DNA-template processes, such as transcriptional activation, DNA replication, repair, recombination and segregation. The methods can be employed with plated cells, suspension cells and with samples of organs, tissues, tumors or other suitable tissue types.

The methods described herein also are useful in clinical investigation and diagnosis. They may be used to unveil the role of covalent histone modifications in cancer development and other human diseases (see, for example, Sassone-Corsi P. et al. Science (1999)). Changes in histone modification may be studied as potential markers for disease. Isolated and/or clinically propagated cells, biopsies or other tissue samples may be subjected to the methods described herein in order to examine patterns of covalent modification of H3, H4 and H1 histone proteins.

As used herein, "chromatin" refers to the nucleoprotein structures present in cell nuclei, comprising DNA and histone proteins, among other constituents. By a "fraction" of chromatin, it is meant an isolatable portion of chromatin, which can include and/or consist of nucleoprotein, nucleic acid or protein. In the context of the present invention, six chromatin fractions may be produced, depending on how far the described methods are taken. The first chromatin fraction produced is nucleoprotein containing predominantly DNA wound around an H3/H4 tetramer, with some H1 protein remaining associated with the chromatin. Upon extraction with acid and precipitation, the second and third chromatin fraction described herein is a mixture of isolated H3 and H4 histone proteins, with or without some isolate H1 histone protein, respectively. The fourth, fifth and sixth chromatin fractions are either isolated H3 histone protein, isolated H4 histone protein or isolated H1 histone protein.

The described methods are the first examples of single-step histone protein extraction from intact, living cells, preserving the original pattern of H3/H4 post-translational modification. There is no need for nuclei isolation, chromatin DNA digestion and chromatographic or gradient ultra-centrifugation steps. The methods are useful for bulk isolation of histone proteins, e.g., histones H3/H4, avoiding generation of possible artifacts and loss of post-translational modifications. The methods permit analysis of bulk metabolically-labeled histone modifications (for example and without limitation, phosphorylation, from $^{32}$P-orthophosphate or acetylation from $^{14}$C- or $^3$H-acetate) by conventional SDS-PAGE, without the need for expensive and complicated techniques such as reverse-phase HPLC to separate the histones. The highly phosphorylated H2A and other low molecular weight phosphoproteins can be removed by certain of the methods described herein, avoiding overlapping and overwhelming of less phosphorylated H3/H4. The methods are quantitative compared to semi-quantitative detection of histone phosphorylation by immunoblotting; and it avoids the problem of epitope occlusion by other modifications in the nearby vicinity of the phosphorylated residues.

The methods are fast, permitting simultaneous processing of analytical or preparative quantities of larger number of samples, e.g., from cells treated with inducers of H3 hypo- or hyper-phosphorylation. They permit kinetics analysis of in vivo fluctuations of, e.g., H3 and H4 modifications in response to environmental changes. Large-scale histone extraction for proteome analysis using mass spectrometry, microsequencing and two-dimensional electrophoretic gels is facilitated by the methods described herein. Large yields of highly pure histone proteins for biochemical and biophysical studies (chromatin assembly, transcriptional studies, and single molecule studies of chromatin dynamics) may be obtained.

The methods are very inexpensive to perform, with a miniscule cost per sample. They are fast and scalable, allowing recovery of milligrams quantities of, e.g., H3/H4 for proteomic analysis. Lastly, the methods are simple, with little requirement for complex materials. One single solution is required during the cell lysis and washes.

As stated above, according to a first embodiment in which cells are lysed in a chaotropic reagent, intact cells are contacted with a solution containing a chaotropic reagent in sufficient concentration to halt substantially all enzymatic processes in the cells and dissociate most of the cellular components but H3, H4 and some H1 histone protein. Useful chaotropic reagents include, without limitation, urea, thiourea, guanidium isothiocyanate (guanidium SCN), guanidium HCl and LiI. Mixtures of chaotropic reagents may be employed. In one non-limiting embodiment, the chaotropic reagent is 8M urea. As a test for the ability of a given chaotropic reagent to halt enzymatic activity and to dissociate contaminating cellular components, the isolation of histone H3 and H4 according to the methods described herein utilizing the given concentration of the given chaotropic reagent in a lysis/wash solution should be able to retain phosphorylation of the histone H3 and/or H4 proteins recovered by the process in quantities similar to or better than that retained by a control experiment using the same lysis/wash solution except the control solution contains, for example, 8M urea, rather than the given chaotropic agent. In terms of quantitative yield and qualitative analysis, a "quantity similar to or better than that obtained in a control experiment" means that the quantitative yield or phosphorylation (for example) is greater than about 10%, preferably greater than about 50% and most preferably greater than 90% of that of a control experiment.

The salt component of the lysis and wash solution typically is a highly or fully ionized salt, for example and without limitation an inorganic salt. By "fully ionized," it is meant a salt that in water, is completely or substantially completely ionized. The salt may be a salt comprising, without limitation, one or more of the following ions: Mg, Ca, Na, K, Li, $NH_4$, $SO_4$, acetate, Cl, F, Br, I, phosphate, bicarbonate and borate, or mixtures thereof. Specific salts include, without limitation, NaCl, KCl, LiCl and $NH_4Cl$. As with the chaotropic reagents other than urea, salts other than NaCl can be tested for efficacy in any given concentration by substituting the NaCl component of the lysis and wash mixture described in the experiments herein with the given salt at the given concentration and yield of histone H3 and H4 and covalent modification of those proteins shall be similar to or better than yields and quality obtained by using 8M urea and an appropriate concentration of NaCl.

The salt either may be present in the lysis buffer that is added to the cells. In one alternate embodiment, the cells are lysed in a lysis buffer comprising the chaotropic reagent, but the salt is added to the resultant cell lysate at a point of time after lysis. The lysis buffer typically has a pH in the range of 7 through 9, though pH values outside of this range are acceptable so long as the lysis buffer remains effective in its desired function.

In certain embodiments, e.g., described in the examples below, once the cells are lysed, they are placed in a tube and then centrifuged and washed in that same tube. The ubiquity of "Eppendorf" tubes makes this process quite easy, using inexpensive and readily-available lab-ware and equipment. Nevertheless, some steps, such as the washings, may be performed on a filter membrane, such as, without limitation, Whatman VectaSpin centrifuge filters and Millipore Microcon and Ultrafree products.

In yet another embodiment, cell lysate produced by lysing the cells in a solution comprising the chaotropic agent is adsorbed onto hydroxyapatite (HA), which in suitable salt concentrations has an affinity for DNA, but not for proteins. Suitable salts include, without limitation NaCl and a mixture of $NaH_2PO_4$ and $Na_2HPO_4$, as well as other salts, so long as they are useful for the intended purpose. Use of HA carrier can facilitate automation of the methods described herein because manipulation of the chromatin pellet is much easier when it is bound to a substrate. Any non-sequence-specific DNA adsorbing material, including, without limitation: calcium phosphates, such as, without limitation, HA, and ion exchange resins, such as, without limitation, DEAE, Mono-Q (Amersham), Toyopearl Super-Q (Tosoh Bioscience). In one embodiment, the DNA adsorbing material is added to the lysate in a centrifuge tube, such as an Eppendorf tube, the material generally facilitating handling of the chromatin. Use of a DNA adsorbing material also will facilitate automation of the process described herein.

Although the examples describe using particular quantities of lysis and wash solutions, there is no fixed amount of solution or ratio of solution as compared to the number of cells used, so long as the amount of solution is not too low so as to prevent efficient lysis and extraction, or too high to be either physically unmanageable. In any case, relative yields of H3 and H4 proteins using different amounts of lysis and/or wash solutions can be readily determined by Coomassie staining as shown in the examples, below.

Once chromatin is prepared containing substantially only H1, H3 and H4 histone proteins, the protein component may be extracted from the chromatin by a number of methods. For example and without limitation, the protein component of the chromatin can be extracted by treatment with an acid, such as, without limitation, $H_2SO_4$ or HCl; by using a detergent, such as SDS; by using higher salt concentrations; or by using organic solvents, such as ethanol, or combinations thereof. In one embodiment, a solution of from about 0.1M to about 0.2 M $H_2SO_4$ is used.

According to yet another embodiment, a method of isolating histone proteins from cells is provided, which comprises lysing the cells in an acid to produce a lysate, neutralizing the acid, binding the lysate to a cationic exchange material at a salt concentration at which histone proteins bind to the cationic exchange material, washing the cationic exchange material and eluting one or more histone proteins with an elution solution having a salt concentration sufficiently high to elute the one or more histone proteins. The acid may be any acid useful for the purpose, for example and without limitation $H_2SO_4$, typically in the range of 0.1 M to 0.25 M, and for example and without limitation, 0.1 M or 0.2 M.

The cationic exchange material typically is a cationic exchange resin. In one non-limiting embodiment, the cationic exchange material is a sulfopropyl agarose, such as SP-Sepharose, as described below. In one embodiment, the salt is NaCl. The method comprises eluting histone proteins from the cationic exchange material with amounts of salt, such as NaCl, effective to elute a desired histone protein fraction from the cationic exchange material. The concentration of the salt used in the elution solution determines which histone fraction is eluted. Typically the lysate is bound to the cationic exchange material at a lower ionic concentration, at which all histone binds to the material, for example and without limitation, 0.1 to 0.5 M NaCl, or 0.2 M NaCl. Alternately, the lysate can be bound to the cationic exchange material at an ionic strength that permits only core histones (e.g., 0.6 M NaCl) or H3/H4 histones (e.g., 0.8 M to less than 2.0 M NaCl) to remain bound to the cationic exchange material. The cationic exchange material can be washed with a salt solution effective to remove most non-histone proteins, but not to elute a desired histone fraction, such as histone H1, which, of the histone proteins, elutes at the lowest salt concentration, for example and without limitation with 0.6M NaCl. Once washed, H1 histone can be eluted with an elution solution having a salt concentration effective to elute histone H1 protein, but essentially not other histone proteins (in other words, the salt concentration is high enough to elute H1, but the predominance of other histone proteins remain bound to the cationic exchange material). Histone H1 may be eluted with 0.6M NaCl.

Once histone H1 is eluted, or even before it is eluted, core histones or core histones plus H1 (if H1 is not previously eluted) can be eluted from the cationic exchange material with an elution solution having a salt concentration effective to elute the core histones from the cationic exchange material. For example and without limitation, NaCl in a concentration of greater than 1M, for example 2M NaCl, can be used for this purpose. To selectively elute histone H2A and H2B proteins, a (first) elution solution can be utilized having a salt concentration effective to elute histone H2A and H2B proteins, but essentially not histone H3 or H4 histone proteins. The (first) elution solution may comprise NaCl in a concentration ranging from 0.7M to 1M, for example and without limitation 0.8M NaCl. Optionally, after eluting the histone H2A and H2B proteins, histone H3 and H4 proteins can be eluted with a second elution solution having a salt concentration effective to elute histone H3 and H4 proteins, NaCl in a concentration of greater than 1M, for example 2M NaCl.

These methods are capable of isolating preparative quantities of chromatin fractions containing H3 and H4 histone proteins, as well as H3 and H4 histone proteins from small amounts of cells. The cells may be plated cells and the methods are implemented as described herein. The cells may be suspended cells, which would need to be spun down and resuspended in lysis solution and very gently rocked for at least the initial few minutes of lysis in order to ensure adequate dispersal of the lysis solution among the cells. Tissue samples may be homogenized directly in the lysis solution (the chaotropic agent in a first method, or an acid in a second method), for example, and without limitation, in essentially the same manner one would homogenize a tissue sample in guanidine SCN to isolate RNA—a widely-known method.

The methods described herein may be implemented manually. That is, all fluid transfer, scraping, aspirating, resuspending, washing and precipitating steps may be performed by a minimally trained technician on a lab bench, so long as that technician has access to a suitable centrifuge and disposable lab-ware (for example, Eppendorf tubes, scrapers and micropipetters), as described herein. Nevertheless, other equipment and lab-ware may be implemented to facilitate the methods described herein. For example, and without limitation, the lysed cells may be centrifuged in a suitable tube, and the chromatin pellet may then be transferred to a centrifuge filter with a very high mw cutoff (100 Kd or higher) and the chromatin then could be washed substantially as described herein, with a spin between washes. Any one or more steps of the protocol may be partially or fully automated using a robotic and/or automated or semi-automated fluid handling device, such as the BioMEK® workstations, commercially available from Beckman Coulter, Inc. of Fullerton, Calif.

In one embodiment, once the H3 and H4 histone proteins are isolated according to the methods described herein, the two proteins can be separated by a number of methods. First, according to one embodiment, by using anti-histone H3 or anti-histone H4 antibodies or other binding reagents affixed to a solid support (for example, and without limitation, beads), the proteins may be separated according to known methods by affinity chromatography.

The term "binding reagent" and like terms, refers to any compound, composition or molecule capable of specifically or substantially specifically (that is with limited cross-reactivity) binding another compound or molecule, which, in the case of immune-recognition contains an epitope. Typically, the binding reagents are antibodies, preferably monoclonal antibodies, or derivatives or analogs thereof, including without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv) fragments), diabodies, tribodies or tetrabodies, which typically are covalently linked or otherwise stabilized (i.e., leucine zipper or helix stabilized) scFv fragments. "Binding reagents" also include aptamers, as are described in the art.

Methods of making antigen-specific binding reagents, including antibodies and their derivatives and analogs and aptamers, are well-known in the art. Polyclonal antibodies can be generated by immunization of an animal. Monoclonal antibodies can be prepared according to standard (hybridoma) methodology. Antibody derivatives and analogs, including humanized antibodies can be prepared recombinantly by isolating a DNA fragment from DNA encoding a monoclonal antibody and subcloning the appropriate V regions into an appropriate expression vector according to standard methods. Phage display and aptamer technology is described in the literature and permit in vitro clonal amplification of antigen-specific binding reagents with very affinity low cross-reactivity. Phage display reagents and systems are available commercially.

Because affinity chromatography typically is expensive and may require refrigeration, among other limitations, HS-(sulfhydryl) group(s) of Cys residue(s) of H3 can be targeted for reversible or irreversible cross-linking to a support (a surface or other substrate, for example and without limitation a bead). A variety of suitable cross-linkers, matrices and cross-linking strategies may be implemented using products commercially available from Pierce and Sigma-Aldrich catalogs, many of which are broadly used. In one embodiment, H3 histone protein is irreversibly bound to a bead. In another, it is reversibly bound such that the covalent linkage between the H3 protein and the substrate to which it is bound may be broken. Reversible binding of the H3 protein permits pass-through of the un-bound H4 protein, and subsequent elution of the H3 protein using a reagent capable of breaking the H3-substrate bond, for example and without limitation a reducing agent such as, without limitation, β-mercaptoethanol (βME), dithiothreitol (DTT) or TCEP (Tris(2-carboxyethyl)phosphine).

In one embodiment, a sample comprising H3 and H4 histones prepared in the manner described herein, histone preparations comprising histone H3 and H4 proteins (e.g., prepared as described herein or otherwise) in a chaotropic agent, are passed over a column or otherwise adsorbed to, preferably, an excess of a surface-bound sulfhydryl-binding compound (a sulfhydryl-reactive group), such as, without-limitation, maleimide, haloacetyl or pyridyl disulfide surface-modified beads. The proteins in the sample can be denatured in an amount of chaotropic agent to denature protein in the sample. Use of EDTA in one or more steps in the purification of H3 from cells may be preferred in many instances to prevent oxidation of the —SH groups in Cys residues. H4 is then washed off the surface (for example, beads), leaving H3 bound to the surface, either irreversibly if the surface is maleimide- or haloacetyl-modified. If the H3 is reversibly bound to the surface, for example and without limitation, by reaction with pyridyl disulfide-modified beads, producing a disulfide bond, a reducing agent such as, without limitation, βME, DTT or TCEP.

The following are non-limiting examples of methods of attaching H3 histone protein to a solid support, such as a bead. It may be preferable in some instances to react any bifunctional compounds first with the support material, block any remaining free reactive sites on the support material, and then bind the support/crosslinker to the H3 protein.

Variant I: LC-SPDP (N-Succinimidyl-6-(3'-(2-pyridyldithio)-propionamido)-hexanoate)

React heterobifunctional LC-SPDP through NHS to a solid support containing primary amines (—NH2) and then couple the pyridyldithio moiety to SH-CysH3. The support could contain a broad range of compounds, including, without limitation: lysine, basic proteins containing lysines, aliphatic primary amines, such as diaminodipropylamine (DADPA), (Pierce), and epsilon-aminohexyl-Sepharose (Sigma-Aldrich)). The reaction should be performed in buffers that would not react with LC-SPDP, such as bicarbonates, acetates, phosphates, borates and other buffers that do not contain sulfhydryl or primary/secondary amine groups.

The H4 will be recovered in the supernatant. H3 can be separate from the solid support by reducing the S—S linkage.

Alternatives to LC-SPDP are SPDP (N-succinimidyl-3-(2-pyridyldithio)-propionate) and sulfo-LC-SPDP (sulfosuccinimidyl-6-(3'-(2-pyridyldithio)-propionamido)-hexanoate).

Variant II: PDPH (3-(2-Pyridyldithio)propionyl hydrazide)

React heterobifunctional PDPH trough the pyridyl disulfide group to SH-CysH3, then couple PDPH through hydrazide to a solid support containing oxidized carbohydrate (Periodate oxidized agarose beads, Sigma-Aldrich, catalog # P9967). The reaction should be performed in buffers that would not react with PDPH or the matrix, such as borates, etc. The H4 can be recovered in the supernatant.

H3 can be separate from the solid support by reducing the S—S linkage.

Variant III: Activated Thiol Sepharose 4b and Thiopropil-activated agarose (Sigma-Aldrich, cat # T8512; T5024)

This is a simpler method because the reactant sulfhydryl group is already immobilized to a solid support. React H3 with the beads in buffer excluding SH groups (phosphate, borate, bicarbonates, etc). Collect H4 in the supernatant and recover H3 from the support with DTT or any other reducing agent.

Variant IV: SMPT (4-Succinimidyloxycarbonyl-methyl-a-[2-pyridyldithio]toluene) bifunctional reversible crosslinker has the advantage to react with S—S groups without previous reducing the S—S linkage.

First, couple SMPT to a support containing a primary amino group (for example and without limitation, diaminodipropylamine (DADPA, Pierce, epsilon-aminohexyl-Sepharose, Sigma-Aldrich). Second, couple the SH group on H3 to 2-(pyridyldithio)toluene. Third, collect H4 in the soluble fraction. Lastly, elute H3 using a reducing agent (e.g., DTT or βME).

In a further embodiment, in preparation of the H3 and H4 histone proteins from chromatin as described herein, the H3 and H4 histone proteins are extracted from DNA, typically by acid extraction, for example and without limitation, by treatment with $H_2SO_4$, as shown in the examples below. H1 histone protein typically is present in the acid-extracted H3 and H4 proteins. As is shown below, precipitation of the H3 and H4 histone proteins with TCA, results in co-precipitation of any remaining H1 histone proteins. Precipitation in, for example and without limitation perchloric acid ($HClO_4$), precipitates the H3 and H4 proteins, but H1 histone protein remains in the supernatant in certain concentrations of perchloric acid, for example and without limitation, about 5% perchloric acid. Once the H3 and H4 proteins are pelleted, the H1 histone protein can then be precipitated, for example and without limitation in TCA, in one embodiment 20% TCA in water, and re-suspended for analysis.

In the commercialization of the methods described herein, certain kits for facilitating the methods described herein are provided. A kit typically comprises a package containing a solution comprising a chaotropic agent and a salt each in an amount effective to lyse cells and an indicia, for example and without limitation, a writing, illustration, label, book, booklet, tag and/or packaging insert, providing instructions relating to one or more of isolation of a chromatin fraction containing H3 and H4 histone proteins using the solution and isolation of one or both of H3 and H4 histone proteins using the solution. As is readily apparent, the literal language provided on the indicia, including, without limitation: spelling, grammar, sentence structure and wording can vary greatly and still indicate that the components of the kit can be used for the stated purpose. The indicia may be packaged, displayed or otherwise distributed or made available separately from the reagents, for example and without limitation, as part of a catalog, advertising brochure, web-site, technical article or technical manual. As used herein, "packaging materials" includes any article used in the packaging for distribution of a drug composition, including without limitation containers, vials, tubes, bottles, pouches, blister packaging, labels, tags, instruction sheets and package inserts.

The kit may comprise a container containing a solution comprising a chaotropic agent and a salt each in an amount effective to lyse cells and to prepare histone chromatin fractions according to a method described herein and an indicia providing instructions relating to one or more of isolation of a chromatin fraction containing H1, H3 and H4 histone proteins using the solution and isolation of one or more of H1, H3 and H4 histone proteins using the solution. The kit may further comprise on or more of a wash solution comprising a chaotropic agent and a salt; a surface comprising one or more of a binding agent specific to H3 histone, a binding agent specific to H4 histone, and a sulfhydryl-reactive group; a non-sequence-specific DNA adsorbing material and a centrifuge filter.

The following examples demonstrate specific embodiments of the present invention and are not intended to limit the scope of the present invention.

EXAMPLE 1

Protocol for Extraction of Histones H3 and H4 from Intact Cells

The following protocol was used to isolate histone H3 and H4 proteins from cells. This protocol is not intended to be limiting and variations of the protocol may be employed with success. These variations include insubstantial modifications of timing, concentrations of reagents, temperature, shaking or other motion of solutions, aspiration methods, pipetting methods, pellet resuspension methods, etc.

Grow cells to about 40-80% confluence in appropriate medium. The cells may be adherent or in suspension cells, though for the present example 90 mm or 35 mm dishes are employed that contain adherent cells in DMEM, 10% Bovine Fetal Serum, 10 unit ampicillin/streptomycin. Medium is discarded that the cells were washed 3 times with 10 ml (90 mm dish) or 2 ml (35 mm dish) of pre-warmed (37° C.) serum and protein-free DMEM. Other medium may be used for washing, so long as it is protein-free. This step ensures minimum disturbance of the native state of histone modifications. Unless otherwise stated, all operations are performed at room temperature (about 25° C.).

With a Pasteur pipette connected to vacuum, completely aspirate any remained wash medium. For initial screening to identify optimal salt concentrations, from about 0.8 ml to about 2 ml (90 mm dish) or about 0.4 ml (milliliter) to about 0.8 ml (35 mm dish) of a solution containing 8 M urea, 20 mM Tris-HCl, pH 8.0 and 0.01M, 0.1M, 0.2M and 0.4 M NaCl) (solution A). Different concentrations of NaCl are used for an initial screening for maximum recovery and purity of the final product (H3/H4). Typically, 0.2-0.4 M NaCl yields good recovery and purity of H3/H4 for many cell lines, such as mouse embryonic kidney cells (see, e.g., FIG. 3), NIH-3T3 (see, e.g., FIG. 4A), HeLa—S3 (see, e.g., FIG. 4B), CHO and breast carcinomas cells (data not shown and see FIG. 2). In other cells lines, for example, diploid normal fibroblast 5659 (FIG. 2) and 5759 (data not shown), H3/H4 are recovered in a solution containing 0.01M, 0.1M and 0.2 M NaCl, with high purity and yield, but 0.4M NaCl, partially strips H3/H4 off (see, e.g., FIG. 2, lane 1 (0.4 M NaCl)).

The cells are lysed by gently moving the solution all over the dish surface, for example, either manually or by rocking. Although lysis of the cytoplasmic membrane commences quickly, it is advised to keep the cells in the dish for 45 minutes without scraping them to avoid formation of aggregates of nuclei and chromatin that may affect the purity of the final extracted H3 and H4. Without limitation, the cells may be gently shaken or rocked at this stage.

Using a plastic scraper, cell lysates are collects in a 1.7 ml Eppendorf tube.

The cell lysates are then spun down at 14,000 (14K) rpm (18 Krcf) for 5 min. This step completely lyses the nuclei, collapsing the chromatin in a pellet. The supernatant is removed, and optionally saved for analysis by aspiration using a thin pipette tip, for example and without limitation, a thin 200 μl (200 microliter) tip. It is preferable to avoid touching the chromatin pellet, which can be very sticky. It is preferable not to use a vacuum to aspirate any supernatants in the following steps.

Wash: add 1 ml of solution A containing the desired concentration of NaCl (0.01-0.4 M). Gently, for example and without limitation, by knocking the button of the tube with your finger, detach the chromatin pellet from the button of the tube. Pipetting may preferably not be used in this embodiment to resuspend the pellet. Centrifuge at 14K (18 Krcf) for 3 min. As above, gently collect the supernatant, preferably avoiding touching the chromatin pellet. Preferably, if, by accident, the chromatin pellet is slightly aspirated into the micropipette, gently pipette it back to the solution. Repeat this procedure 5 times with 1 ml solution A.

H3/H4 extraction: add 150 μl (for cells at 40% confluence) or 300 μl (for cells at 80% confluence) 0.2 M $H_2SO_4$ to the chromatin pellet from a 90 mm dish (in the case 35 mm dishes, use 50 μl (40% confluence) or 100 μl (80% confluence). Leave overnight at 4° C. or extract for 2-3 h (until the transparent appearance of the pellet becomes white nontransparent) Shake the tubes, for example and without limitation, with your finger from time to time or until no more protein contaminants come out in the wash according to mini-Coomassie protein assay (Pierce).

Separate the acid-soluble H3/H4 from insoluble DNA at 14K (18 Krcf) for 5 min (keep the insoluble pellet depleted of H3/H4 for analysis, if necessary). Save supernatant containing the histones and precipitate H3/H4 (plus some residual H1) with a final concentration of 20% TCA or precipitate H3/H4 with 5% $HClO_3$ (leaving H1 soluble) on ice for 4 h or overnight.

Collect the histone pellet at 14K (18 Krcf) for 10 min. Discard supernatant. Wash histone pellet once with acetone/0.1% HCl (500 μl) and once with acetone (500 μl). Air dry the pellet. Resuspend the histone pellet in 200 μl (for 90 mm dish, 80% confluence) or 40 μl (for 35 mm dish, 80% confluence) of $H_2O$, containing 10 mM DTT overnight at 4° C., or in SDS reducing sample buffer, or any other chosen solution.

EXAMPLE 2

Isolation of H3/H4 from a Variety of Cell Lines

The flow process for extraction of H3/H4 from intact cells is depicted in FIG. 1. The cells are incubated in 8 M urea containing variable salt concentrations. This preserves the morphology of the cell nucleus for a relatively long period of time (visual microscopic inspection of HeLa and other cells upon urea/salt incubation provides, without limitation, a margin of at least about 45 minutes of nuclei stability), permitting collection by centrifugation at 14K of the tetrasomic H3/H4. Somehow, the inorganic salts maintain the chromatin in a compact structure, rendering it suitable for centrifugation and manipulation. Cell lysis in 8 M urea without salts, provokes an instantaneous swelling of the chromatin DNA, rendering it difficult to manipulate (data not shown).

Figure 2:
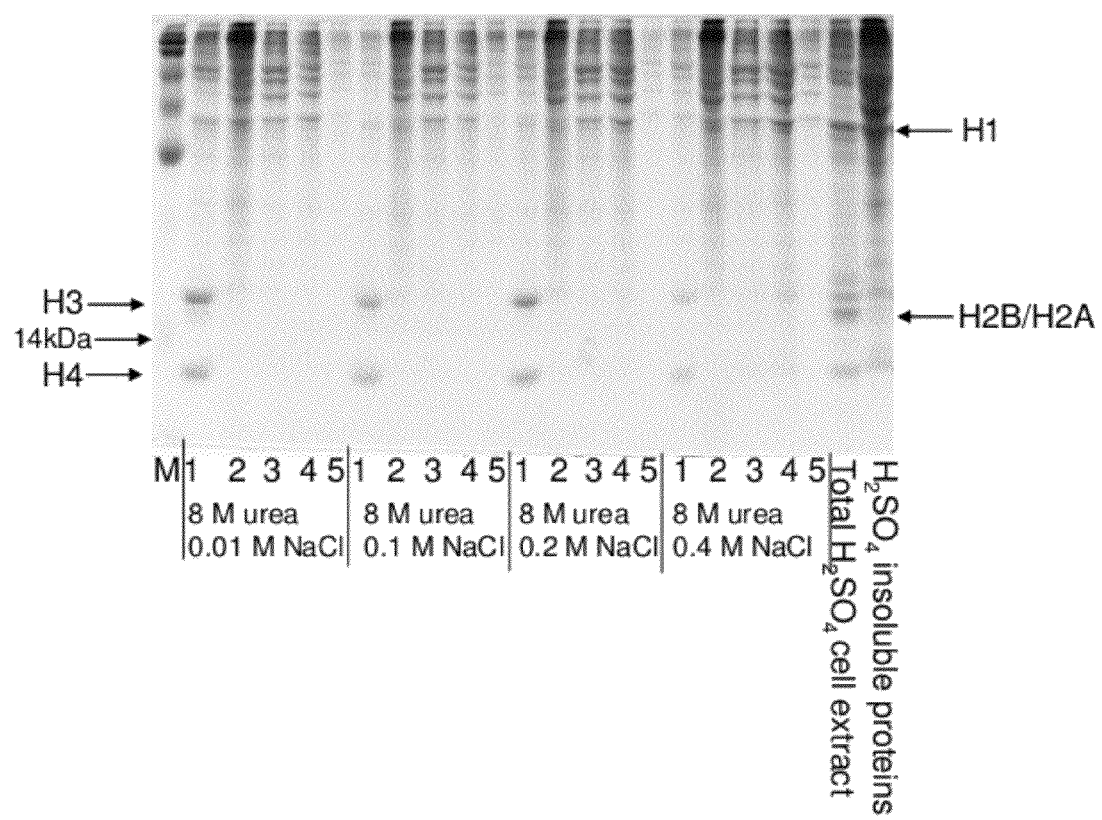
FIG. 2 is a scanned digital image of a Coomassie-stained SDS-PAGE gel showing single-step H3/H4 extraction from normal diploid fibroblast.

After washing, the H3/H4 and some residual H1 (not shown) are acid-extracted and TCA or $HClO_3$ precipitated. Normal human diploid fibroblasts were denatured in 8 M urea containing increasing concentration of NaCl (FIG. 2). Concentrations of NaCl, ranging from 10 to 200 mM NaCl strip most of the H2A/H2B and H1 histones among with other proteins of broad molecular mass (compare lanes 1 with the bulk $H_2SO_4$ extracted histones); thus, the residual acid-extracted histones H3/H4 are suitable for direct isotopic analysis using SDS-PAGE. 0.1 M NaCl gave the highest relative purity for H3/H4, whereas at higher 0.4 M NaCl concentration some of H3/H4 are lost without increasing in their relative purity.

FIG. 2 shows a single-step H3/H4 extraction from normal diploid fibroblast. A 90 mm dish (at 40% confluence) of 5659 cells were extracted with 800 µl of 8 M urea at increasing NaCl concentrations (indicated in the figure) and the samples were analyzed by 15% SDS-PAGE. Lane M contains a molecular weight marker (14 kDa is indicated at the left of the figure). Lane 1 contains 10 µl $H_2SO_4$ extracted H3/H4 after cell homogenization and chromatin washed with 8 M urea and NaCl as indicated on the figure. Lane 2 contains 10 µl of $H_2SO_4$— insoluble proteins. Lane 3 contains 10 µl supernatant of urea/salt solubilized cells. Lane 4 contains 10 µl of the first chromatin wash. Lane 5 contains 10 µl of the second chromatin wash. A loading control (10 µl) for bulk histone was obtained by extracting the whole cells with $H_2SO_4$, as indicated in the figure. The bulk $H_2SO_4$-insoluble proteins are also indicated in last lane of the gel. All samples (except sample 3) were resuspended in equal volumes (40 µl).

Figure 3:
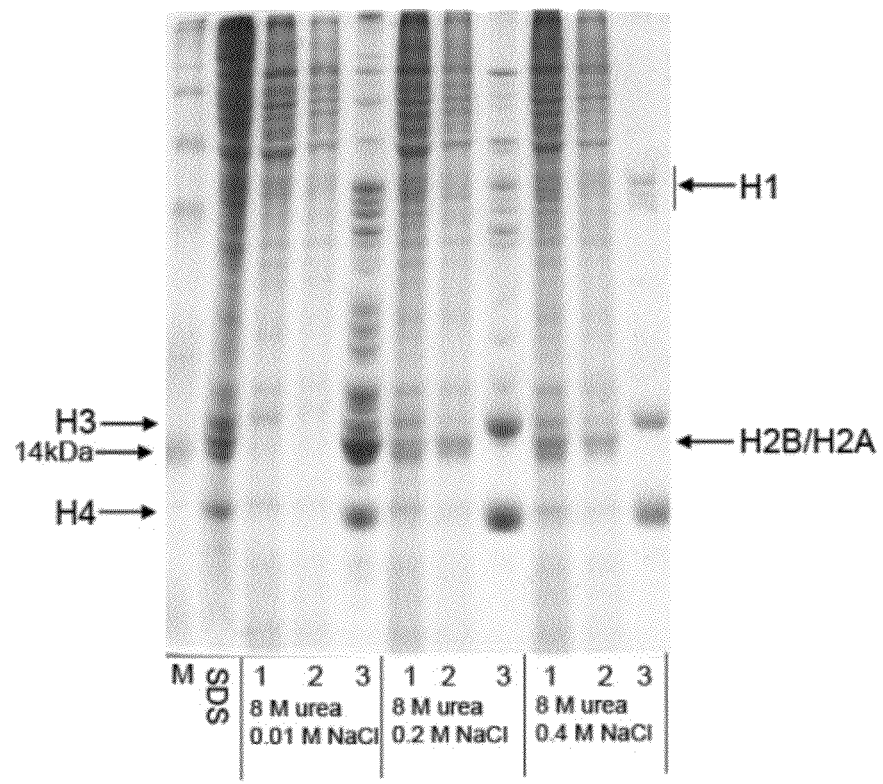
FIG. 3 is a scanned digital image of a Coomassie-stained SDS-PAGE gel showing single-step H3/H4 extraction from mouse embryonic kidney cells.
Figure 4A:
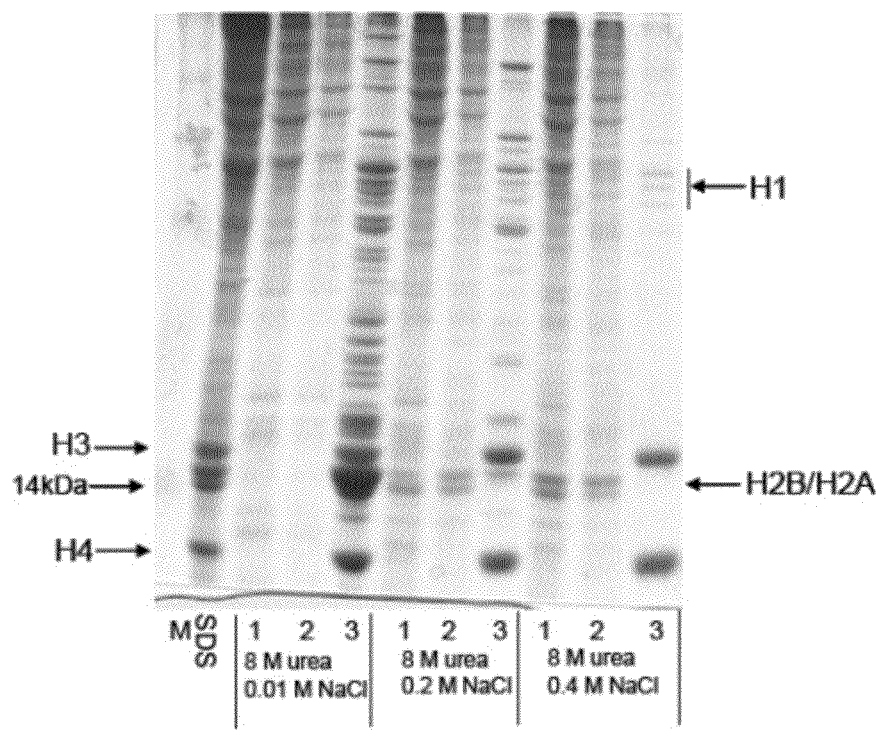
FIGS. 4A and 4B are scanned digital images of Coomassie-stained SDS-PAGE gels showing single-step H3/H4 extraction from NIH-3T3 and HeLa—S3 cells, respectively.
Figure 4B:
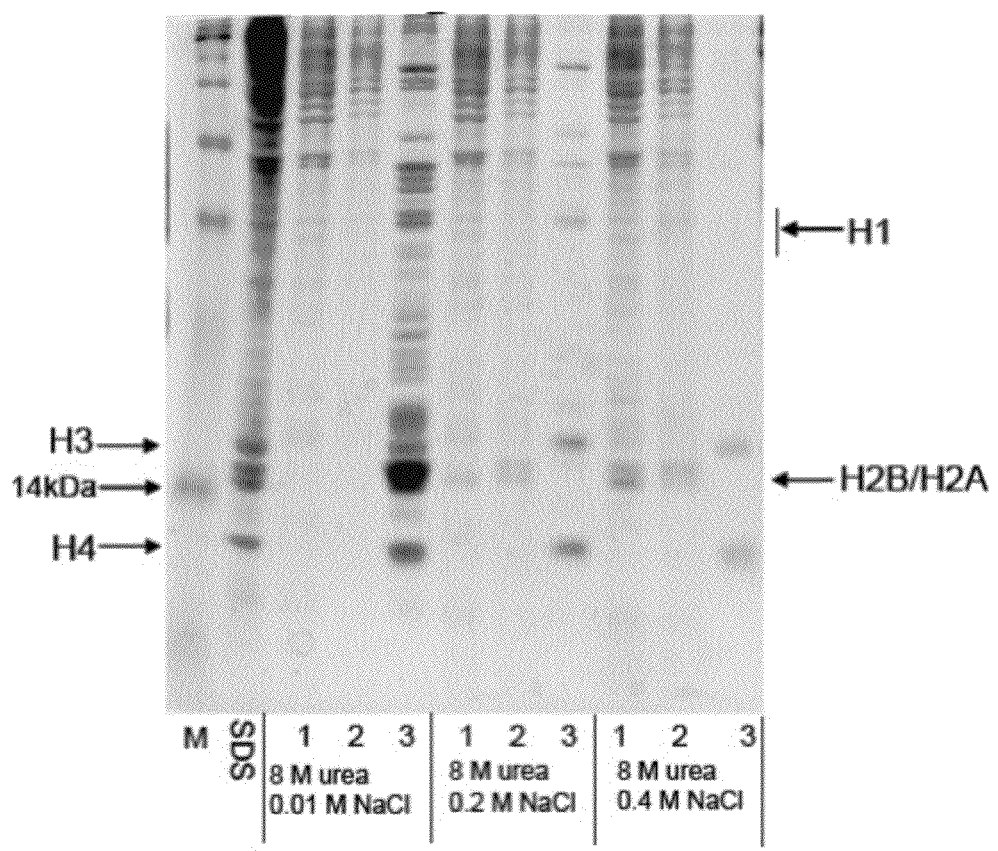

FIGS. 3, 4 and 5 show that the range of salt concentrations for optimal recovery and highest purity for H3/H4 can vary among cell type. Unlike 5659 normal human fibroblast (FIG. 2), H3/H4 from mouse embryonic kidney cells (FIG. 3), NIH-3T3 (FIG. 4A) and HeLa cells (FIG. 4B) cells can be obtained with the highest purity at 0.4 M NaCl (compare lane 3, $H_2SO_4$—H3/H4 extraction following the 8 M urea/0.4 M NaCl wash).

FIG. 3 shows a single-step H3/H4 extraction from mouse embryonic kidney cells. One 90 mm dish of embryonic kidney cells (at 80% confluence) was extracted as described in FIG. 2. All the extract and washes were precipitated with 20% TCA and resuspended in 200 µl reducing sample buffer. 10 µl of each sample was separated by 15% SDS-PAGE and visualized by Coomassie staining. Lane M contains a molecular weight marker (14 kDa is indicated). Lane SDS contains 10 µl of 500 µl of SDS reducing sample buffer of total cell extract (loading control for H3/H4 recovery). Lane 1 contains supernatant of urea/salt solubilized cells. Lane 2 contains the chromatin wash. Lane 3 contains $H_2SO_4$-extracted H3/H4, following five washes of 1 ml each with 8 M urea and NaCl, as indicated on the figure.

FIG. 4 shows a single-step H3/H4 extraction from NIH-3T3 cells. See explanation for FIG. 3.

Although differential extractions of H3/H4 from chromatin arrays (in solution or immobilized to hydroxyapatite or using limited amount of cation exchange resins to capture the striped histones) have been published (Bolund L A, Johns E W. The selective extraction of histone fractions from deoxyribonucleoprotein. Eur J Biochem. 1973 Jun. 15; 35(3): 546-53); we conclusively demonstrated that highly purified H3/H4 can be obtained from a variety of cell lines, in one single step with high yield, bypassing the need for nuclei isolation, chromatin DNA digestion and any chromatographic or gradient-ultra centrifugation of the samples. Previous methods has used low concentrations of urea (3-5 M) to separate H3/H4 from H2A/H2B in chromatin arrays or in solution (Johns E W, et al. Arch Biochem Biophys. 1972; Spelsberg T C, et al. Proteins of chromatin in template restriction. I. RNA synthesis in vitro. Biochim Biophys Acta. 1971 Jan. 1; 228(1): 202-11; Spelsberg T C, et al. Proteins of chromatin in template restriction. II. Specificity of RNA synthesis. Biochim Biophys Acta. 1971 Jan. 1; 228(1): 212-22; Spelsberg T C, et al. Proteins of chromatin in template restriction. 3. The macromolecules in specific restriction of the chromatin DNA. Biochim Biophys Acta. 1971 Jan. 28; 228 (2): 550-62; and Ansevin A T, et al. Structure studies on chromatin and nucleohistones. Thermal denaturation profiles recorded in the presence of urea. Biochemistry. 1971 Dec. 7; 10(25): 4793-803), a condition that may not prevent the activity of hydrolytic enzymes (e.g. phosphatases, deacetylases, demethylases, proteases, etc.), leading to a loss of a given modification and to protein proteolysis. The methods described herein can be performed at both analytical and preparative scales, yielding high-purity H3/H4 histones with excellent recovery, something that previous histone extractions failed to achieve. For example, prior art references cited herein use soluble polynucleosomes, ignoring the insoluble nucleosome arrays. In addition, the solubilization process generates intrinsic instability within the soluble polynucleosomes leading to their aggregation and precipitation. Thus, an important histone fraction will be irremediably lost during solubilization of nucleosomal arrays.

EXAMPLE 3

H3 Phosphorylation Retention at Different Urea Concentrations in the Lysis/Wash Solution Previously, low concentration of urea (<5 M) had been used to extract H3 and H4 from nuclease digested and relatively pure chromatin arrays (Johns E W, et al. Arch Biochem Biophys. 1972 and Johns E. W. Biochem J. 1967). In view of this, a comparison of the ability of 6 M urea versus 8 M urea to preserve the in vivo pattern of histone phosphorylation was performed. In addition, the ability of 8 M urea and salt to extract highly phosphorylated H3/H4 histones also was assessed, with high yield and purity obtained from mitotically arrested HeLa S3 cells. To achieve maximum phosphorylation of histone HeLa cells were synchronized in metaphase using 1 µg/ml nocodazole for 20 hours. Extracts with either 6 or 8 M of urea were separated by 15% SDS page and the levels of Ser10 phosphorylation (a classic mitotic marker, were compared in immunoblots by using an anti-phospho-histone H3 (Ser 10) antibody (rabbit polyclonal, Upstate, N.Y.). In addition, logarithmically growing HeLa cells (containing low levels of phosphorylated histones) were hypotonically treated with $H_2O$ diluted PBS (4:1 v/v) for 20 min at room temperature. This treatment yield hypophosphorylated histones that will serve as a reference to compare hyperphosphorylated H3/H4, extracted with either 6 or 8 M urea, from mitotically arrested cells. It was noted that the hypotonically treated cells were more resistant to lysis by urea. The incubation time in the lysis solution for those cells was 2.5 hours at room temperature. The lysed cells were then spun down and the chromatin was recovered in the pellet for subsequent washes and histone extraction (see described protocol). Conversely, the mitotically arrested cells lysed quite easily (3 minutes or less) and once the cell membrane was lysed a rapid spin was performed to keep the chromatin tightly packed. Then the lysed cells containing the bulk of H3/H4 bound to the chromatin were kept in the same lysis solution (6 or 8 M urea) for 2.5 hours to determine the effect of phosphatases on serine 10.

Figure 5A:
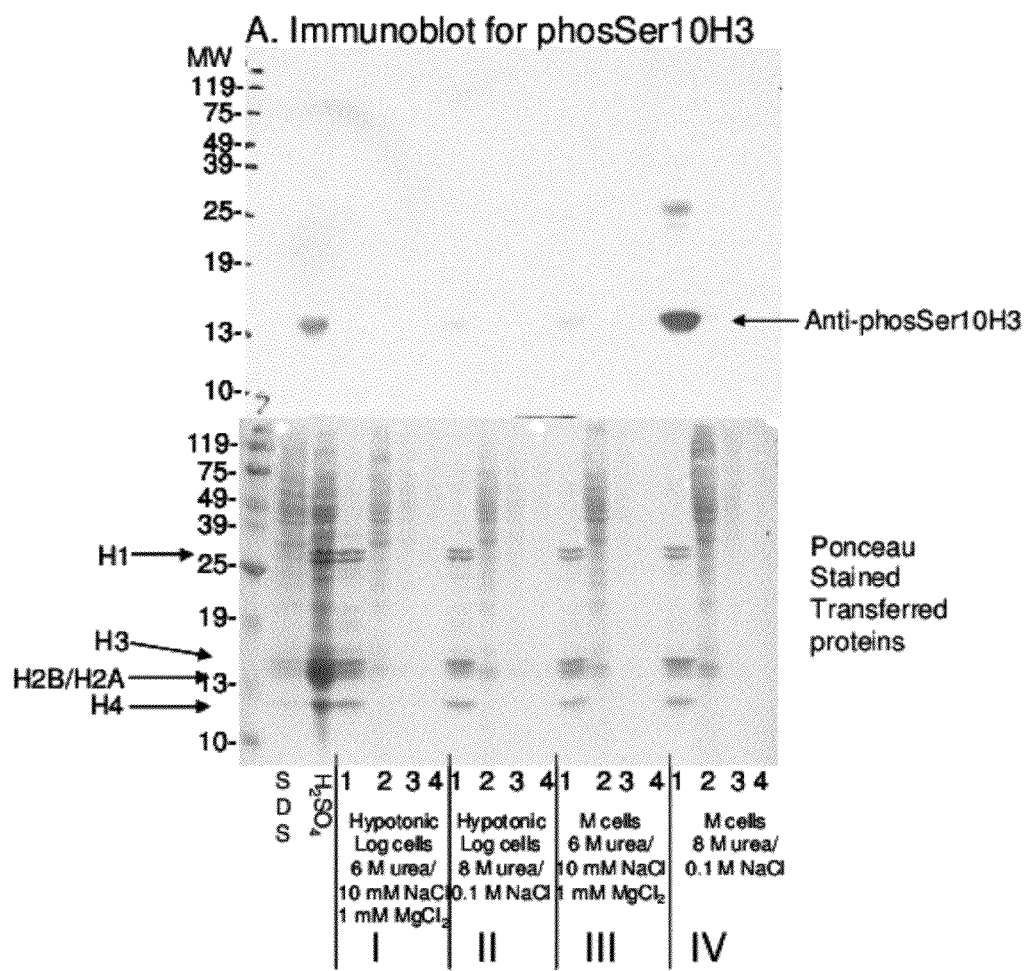
FIG. 5A is a chemiluminescent signal (top panel) showing immunoblotting for Ser10 H3 after extraction with either 6 or 8 M urea and a photograph (bottom panel), showing Ponceau staining of proteins demonstrating similar protein loading and transfer.
Figure 5B:
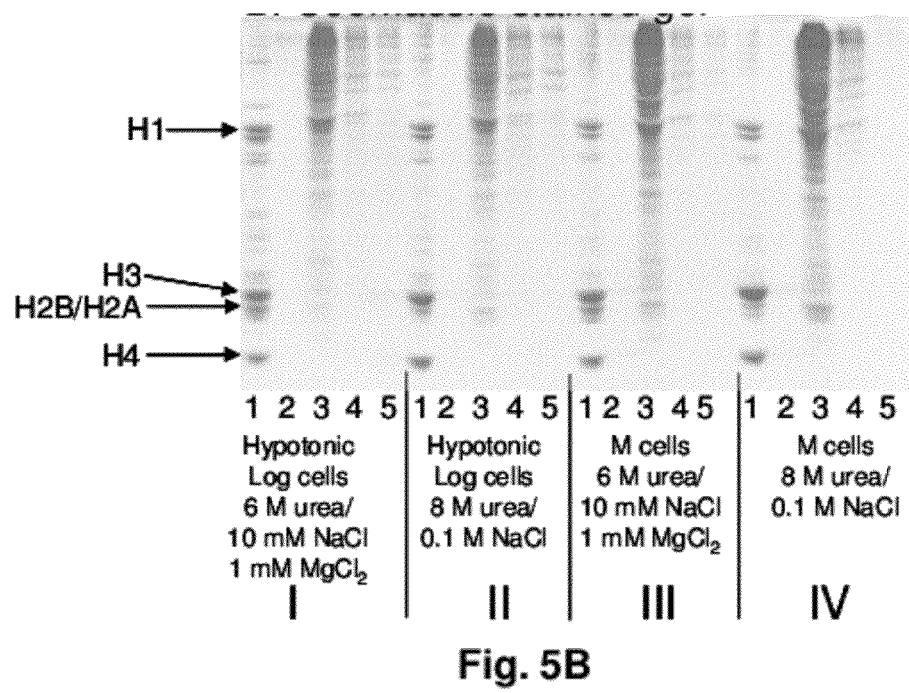
FIG. 5B is a scanned digital image of a Coomassie-stained SDS-PAGE gel showing that 6 M urea dephosphorylated mitotic Ser10 H3, which typically is highly phosphorylated, and how 8 M urea preserves the phosphorylated Ser10 H3.

FIG. 5B shows that 6 M urea (compare lane 1 (III) with 8 m urea M-phase cells lane 1 (IV)) dephosphorylated mitotic Ser10 H3, which typically is highly phosphorylated. This suggests that phosphatase activities are not prevented using lower concentration of urea. Urea, in a concentration of at least about 8M was necessary and sufficient to preserve hyperphosphorylated Ser10 on H3 during the extraction procedure from M-phase cells. Importantly, H3/H4 as well as H1 were quantitatively recovery from metaphase cells (FIG. 5A, lane 1 (III and IV). Note that 0.1 M NaCl was used, which is a sub-optimal concentration to deplete all H2B from this kind of cells. Thus some contamination with H2B and to a lesser extend with H2A is observed (lane 1 (I, II, III, IV). Of note is the presence of H1 in 8M urea containing 0.1M NaCl in HeLa cells. The H1 can be recovered in soluble form by precipitating the rest of the histones in 5% perchloric acid. Then H1 in perchloric acid can be precipitated with 20% TCA.

FIG. 5 shows the effect of urea concentration in preserving the in vivo pattern of histone phosphorylation. FIG. 5A, top panel, shows immunoblotting for Ser10 H3 after extraction with either 6 or 8 M urea. FIG. 5A, bottom panel, shows Ponceau staining of transferred proteins. The Ponceau reversibly stains proteins on membranes, and is very useful to compare the relative amounts of the histones (any protein), thus giving an objective information about the signal produce from the anti-phospho Ser10 H3 antibodies. The histones were separate by 15% SDS-PAGE and blotted to Nitrocellulose. The phosphorylated Ser10 H3 was detected with a rabbit polyclonal antibody (Upstate, N.Y.) after developed with HRP-anti-rabbit (upper panel; lower panel shows the protein loading control as a Ponceau staining). The molecular marker and histone H1, H3, H2B/H2A and H4 are indicated on the left. The condition of H3/H4 (H1) extractions are indicated by roman numbers. The SDS lane contained total HeLa cellular extract in a reducing sample buffer. The $H_2SO_4$ lane contained total HeLa histone extract with 0.1 M sulfuric acid. Lane 1 contains final extracted histones after treatment with urea as indicated on the figure (I-IV). Lane 2 contains urea soluble proteins (note H2B/H2A). Lanes 3 and 4 contain a wash of the chromatin pellet with urea as indicated for I-IV. FIG. 5B shows Coomassie staining of the samples in FIG. 5A, which gives a better evaluation of the quality (purity, composition, etc.) of the extracted histones. The loaded lanes are identical as for FIG. 5A, except that lane 2 is the acid-insoluble material remaining after final extraction of the histones (note that lane 1, 3, 4, 5 correspond to lanes 1, 2, 3 and 4, respectively, in FIG. 5A).

Figure 6:
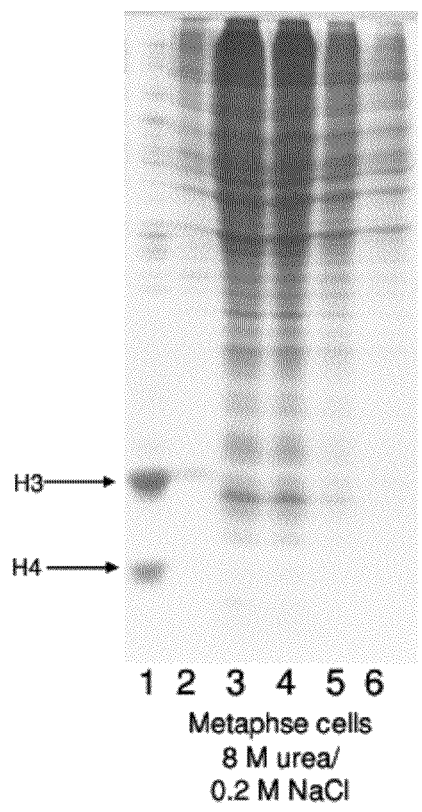
FIG. 6 is a scanned digital image of a Coomassie-stained SDS-PAGE gel showing quantitative recovery of H3/H4 from mitotically arrested HeLa cells after treatment with 8 M urea/0.2 NaCl.

The procedure was re-assessed using a more astringent salt concentration (FIG. 6). 0.2 M of NaCl produced a mitotic H3/H4 preparation almost free of H1 and H2A/H2B, as judged by Coomassie staining (FIG. 6, lane 1).

FIG. 6 shows Coomassie stained, 15% SDS-PAGE showing quantitative recovery of H3/H4 from mitotically arrested HeLa cells after treatment with 8 M urea/0.2 NaCl. The samples are: Lane 1 contains final extracted histones after treatment with 8 M urea/0.2 M NaCl; Lane 2 contains acid-insoluble material after final extraction of the histones; Lane 3, urea soluble proteins (note H2B/H2A); and Lanes 4, 5, 6 contain a wash of the chromatin pellet with the same lysis solution (8 M urea/0.2 M NaCl).

EXAMPLE 4

Recovery of H3 and H4 from Intact Cells by Using Hydroxyapatite and High Urea and Salt Concentrations By using a DNA binding matrix, in this case hydroxyapatite (HA), the manipulation of the chromatin pellet is less difficult. The method also allows use of a column format, since the chromatin is immobilized on HA resin. The method gave high purity and recovery of H3 and H4 from intact 3T3-NIH cells.

Figure 7:
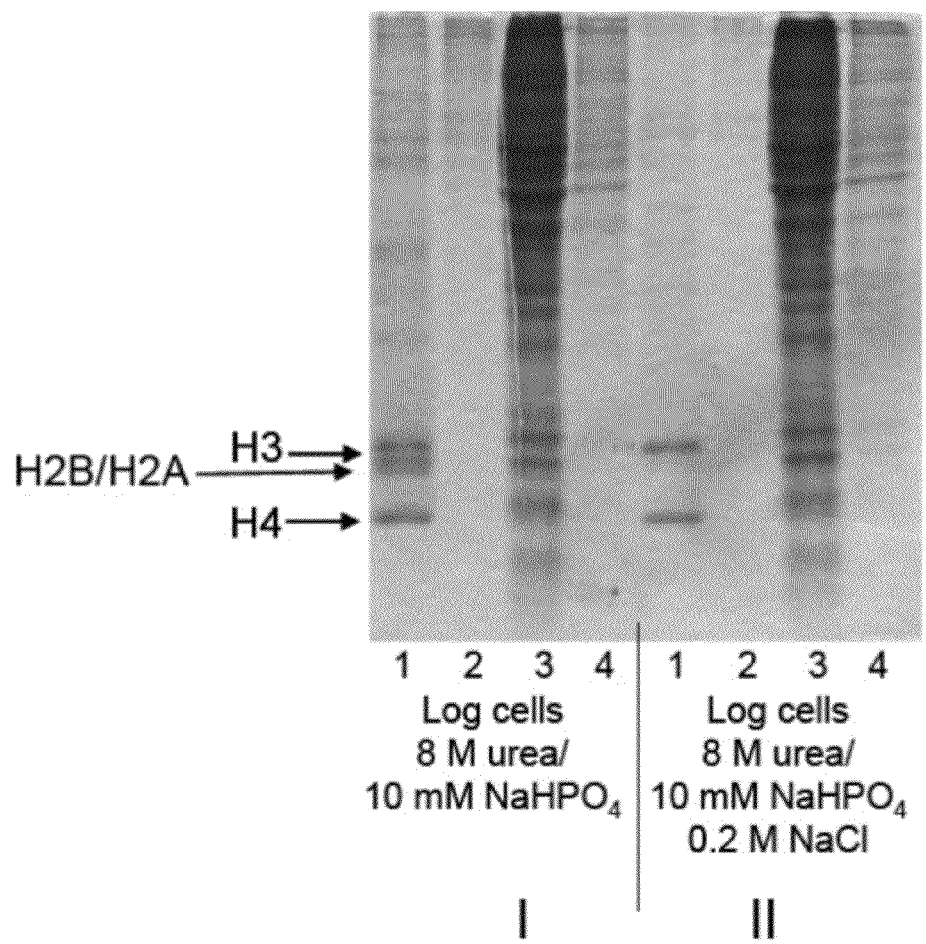
FIG. 7 is a digital scanning of a Coomassie-stained SDS-PAGE gel showing single-step H3/H4 extraction from 3T3-NIH cells using hydroxylapatite support.

FIG. 7 shows recovery of H3 and H4 from intact cells by using hydroxyapatite and high urea and salt concentrations. Confluent 35 mm dish 3T3-NIH cells were incubated in 500 μl 8 M urea/10 mM $NaHPO_4$ (solution I) until the cytoplasm was lysed (monitored by visual inspection under microscope). To one dish was added 0.2 M NaCl (solution II). The lysed cells were spun at 14K RPM (18 Krcf) in a microcentrifuge for 10 min.

To the chromatin pellet and soluble proteins was added 100 μl hydroxyapatite (½5 suspension in solution, as described below in I or II) (BioRad). The mixture was incubated for 10 min at room temperature with rotation (Labquake). The bound chromatin was pellet at 500-1000 rpm in a microcentrifuge. The supernatant was saved for 15% SDS-PAGE analysis.

The bound chromatin was extensively washed with either solution of Experiments I or II, described below, until no more protein could be detected by micro-Coomassie assay (Pierce). The histones were eluted from the bound chromatin in 50 μl 0.2 M $H_2So_4$ overnight at 4° C. All materials were precipitated with 20% TCA for 4 hours in ice. The precipitates were recovered by centrifugation at 14 k rpm, for 20 min. at room temperature. All samples were resuspended in 40 μl reducing sample buffer and 10 μl were loaded in an SDS-PAGE and stained with Coomassie blue.

Experiment I: Lane 1, acid extracted histones (note that since the ionic strength is low, part of H2A/H2B can be recovered). Lane 2, acid-insoluble proteins resuspended in 2× reducing sample buffer. Lane 3, flow-through from the HA matrix. Lane 4, first wash (1 ml).

Experiment II: Lanes are identical to Experiment II, except that the lysis and washes solutions contained 0.2 M NaCl (see FIG. 7).

EXAMPLE 5

Extracted H3/H4 are Functional and form Tetrasomes in the Presence of Chromatin Assembly Factors Of great interest to the scientific community is the relationship between the histones and the DNA, in terms of three-dimensional structure of the chromatin fiber. Within the context of the chromatin, structure is regarded as function. For example, histone acetylation is thought to lose the interaction of the histone N-termini with the DNA, rendering the nucleosome less compacted and accessible to RNA polymerase. Thus, by manipulating such modification gene expression can be change without change the DNA nucleotide sequence (epigenesis) and in many instances, cancerous cells can be reverted to a normal differentiated state (Milin R. et al. Rational development of histone deacetylase inhibitors as anticancer agents: a review. Mol Pharmacol. 2005 October; 68(4): 917-32). On the other hand, global phosphorylation of histones is linked to chromosome condensation and mitosis and deregulation of this process may cause chromosome instability and cancer development (Janssens V, et al. PP2A: the expected tumor suppressor. Curr Opin Genet Dev. 2005 February; 15(1): 34-41, Choi H S, et al. Phosphorylation of histone H3 at serine 10 is indispensable for neoplastic cell transformation. Cancer Res. 2005 Jul. 1; 65(13): 5818-27).

Because this extraction method provides a relatively homogeneous preparation of H3/H4, retaining their original patterns of modifications, the functionality of such histones was assessed. To assess functionality, the extracted histone proteins were tested for their ability to assemble into poly-tetrasomes. To this end, a supercoiling assay was used with partially purified chromatin assembly factors containing NAPs eluted from Q-Sepharose at 500 mM NaCl (QS500) (Rodriguez, P., et al. (2004) NAP-2 is part of multi-protein complexes in HeLa cells. *J. Cell. Biochem.* 93: 398-408). In this method, folded H3/H4 histone protein is deposited onto a relaxed, close-circular plasmid. If functional, the H3/H4 histone proteins would produce a negative supercoiling in the plasmid. This assay serves as a good assessment on the folding state of H3/H4; because unfolded histone will be not able to supercoil the relaxed DNA.

Figure 8:
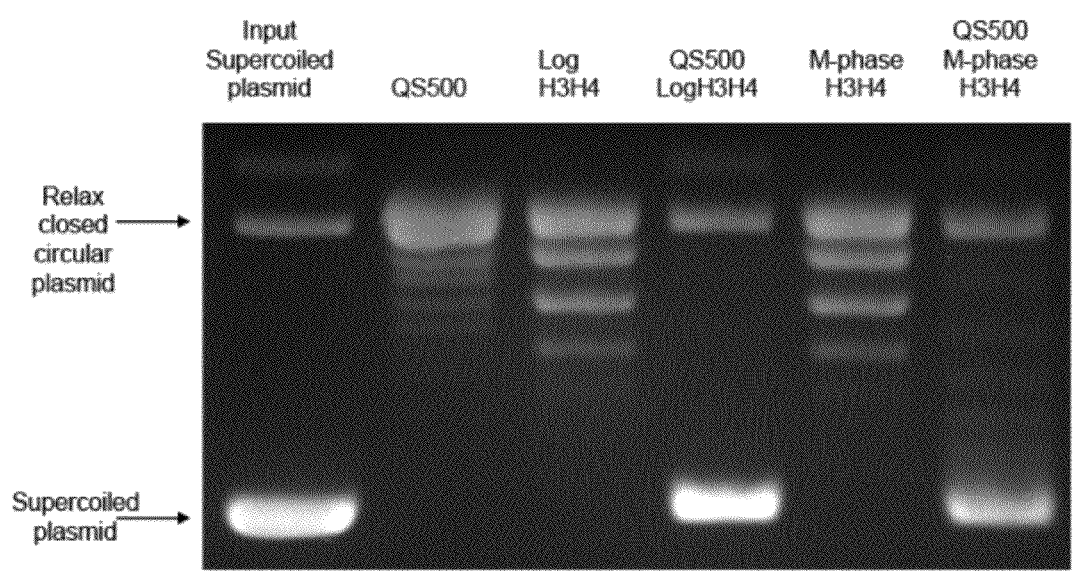
FIG. 8 is a digital image of H3/H4 deposition onto a relaxed-close circular plasmid, and suggests that the tetramer H3/H4 from logarithmically growing and mitotic-arrested HeLa cells are functional.

FIG. 8 shows the supercoiling activity of H3 and H4 extracted from HeLa cells according to one embodiment of the present invention. BlueScript plasmid (6.5 µg) was relaxed with 15 IU of Topoisomerase I (Topo I, Promega) in PBS/1 mM EDTA. 1.25 µg DNA was used for each lane. The QS500 fraction in PBS/1 mM DTT/(10 µl at 6 µg/µl) was pre-mixed with histones H3/H4 (2 µg total) for 15 min at room temperature. The relaxed plasmid was added and the deposition reaction was allowed for 80 min at 37° C. in a final volume of 13 µl. The reaction was stopped with 0.1% SDS (final concentration) and 5 µg proteinase k. The digestion of all protein was prolonged for 1 hour and the SDS and residual proteins were extracted with 10 µl phenol/chloroform/isoamyl alcohol by vortexing. The reaction was run in 0.9% agarose gel/1×TAE.

Preliminary results shows (FIG. 8) that H3/H4 histone proteins extracted from log- and M-phase HeLa cells were able to supercoil relaxed DNA in the presence of a QS500 fraction (compare lanes 4 and 6 with lanes 2, 3 and 5). This deposition depends on the presence of both histone chaperones (QS500) and histones, because the QS500 fraction and the histones by themselves do not have such activity (lane 2, 3, and 5, respectively). This experiment demonstrates that both hypo- and hyperphosphorylated histones can be reconstitute onto poly-tetrasomes and serve as a subject for investigations into histone modification-dependence of chromatin structure and function.

EXAMPLE 6

Purification of Core Histones and H1 in a Single Chromatographic Step Using Sulfopropyl Sepharose (SP Sepharose)

This protocol allows obtaining all core histones from intact cells, preserving their patterns of natural modifications. In addition, this method allows recovery of fractionated H1, H2A/H2B and H3/H4 in a single chromatographic step. The obtained histones can be used for laboratory analysis (in clinical or basic sciences) and in chromatin template processes (e.g. nucleosome assembly and disassembly, transcriptional activation, DNA repair, chromatin condensation and single-molecule approaches. In addition, the histones can be a source for crystallographic studies.

Method

Wash cells with pre-warmed at 37° C. DMEM or any suitable serum-free growing medium.

Extract total histones from metaphase (hypotonically treated or not treated, or log intact HeLa cells (or from any other cells or tissue) with 1 ml 0.1 M (or 0.2M) $H_2SO_4$/3×150 mm dishes at 90% confluent, overnight at 4° C. (or for 1-2 hours). Re-extract pellet if needed. $H_2SO_4$ extraction is most likely to inactivate most of unwanted uncontrolled enzymatic activities. Thus, it will protect the histones and their post-translational modification of being artificially changed.

Neutralized extracted histones with equal volume of 1 M Tris-HCl, pH 8. Optional: To inhibit any residual enzymatic activity that may affect the in vivo pattern of histone modifications, to 1 M Tris-HCl may be added suitable inhibitors against unwanted enzymes (e.g. okadaic acid 200 nM).

Dilute neutralized histones with equal volume of 0.4 M NaCl. Optional: Add 5 M concentrated NaCl to a final concentration of 0.2 M.

Flow crude histones (3×150 mm dish) twice over 1 ml SP Sepharose (0.5×2 cm), equilibrated (10 volume) in 50 mM Tris-HCl, ph 8, 0.2 M NaCl.

Wash SP (10 volume) with 0.5 M NaCl in the same buffer. This step eliminates most of the contaminant proteins.

Wash SP (10 volume) with 0.6 M NaCl, in the same buffer. Collect most of H1 in the first three fractions of 1.5 ml each.

Eluted core histones with 10 ml 2 M NaCl (or 1 M NaCl), in the same buffer. The 2 M salt will allow recovering all core histones highly concentrated, typically in 0.8-1 ml of the first fraction (note that 1 ml resin has a void volume of 0.6-0.7 ml).

Optional: H2A/H2B can be selectively eluted from SP Sepharose (keeping H3/H4 bound to the resin) with 0.8 M NaCl. Then H3/H4 can be eluted with 2 M NaCl in the same buffer.

After elution, the histones can be diluted or dialyzed against any suitable buffer.

Optional: Precipitate all core histones (or H2A/H2B and H3/H4) with 4-5% perchloric acid, overnight at 4° C. This step will eliminate residual H1. Wash 2× (1.5 ml) with the same solution to eliminate salt. Wash acetone/0.1 M HCl. Wash 2× acetone. Dry. Resuspend in any suitable solution.

Results

Figure 9:
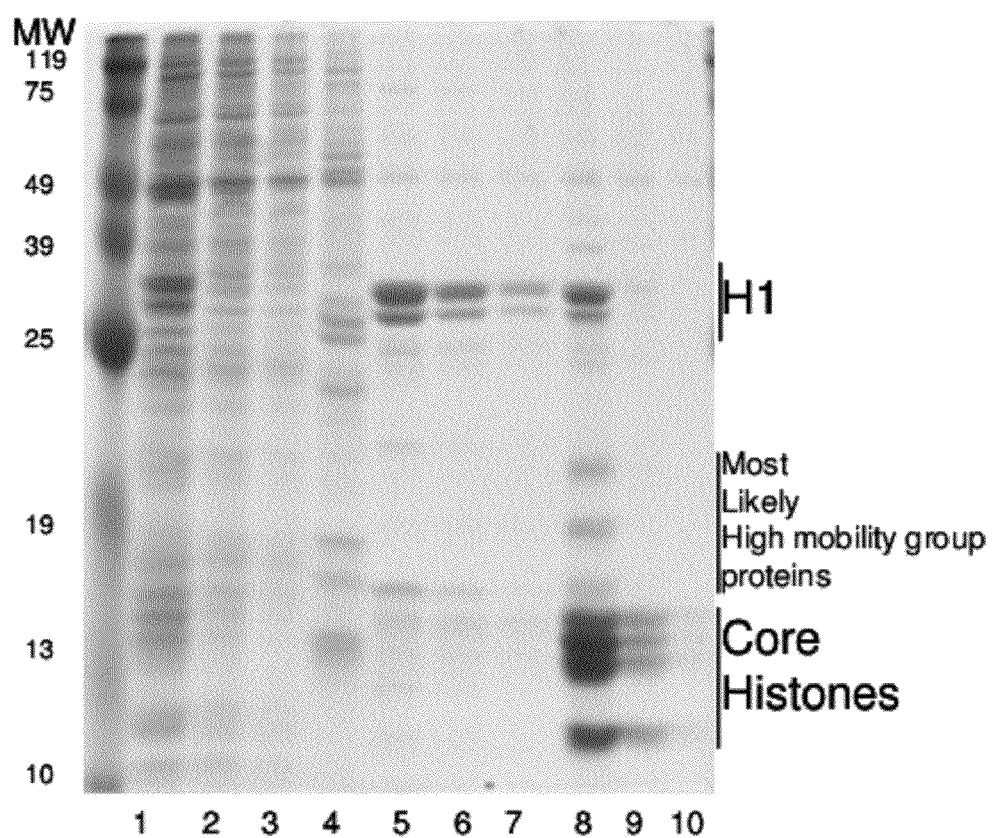
FIG. 9 shows an SDS-PAGE of SP-purified core histones and H1 from mitotically arrested HeLa cells.

FIG. 9 shows an SDS-PAGE of SP-purified core histones and H1 from mitotically arrested HeLa cells. Total histones were extracted with sulfuric acid and bound to SP Sepharose (Sigma). The bound H1 and core histones were washed and eluted stepwise at increasing concentrations of salt. Core histones, H1 and probably HMG proteins are indicated on the figure. Note that that H1 and HMG proteins can be separated from core histone by differential precipitation with 5% perchloric acid (data not shown). Proteins from each step were loaded in the lanes as follows: 1, 20 µl out 6 ml of input $H_2SO_4$ extracted proteins from mitotic HeLa cells (3×150 mm at ~90% confluence). 2, 20 µl out 6 ml SP-flow-through. 3, 20 µl out 1.5 ml wash 0.2 M NaCl, 50 mM Tris-HCl, ph 8.4, as for 3 but wash with 0.5 M NaCl. 5-7, as for 3 but wash with 0.6 M NaCl. 8-10, 10 µl (diluted 1:2 with 2× reducing sample buffer) out 1 ml elution with 1 M NaCl, 50 mM Tris-HCl, ph 8.

Figure 10:
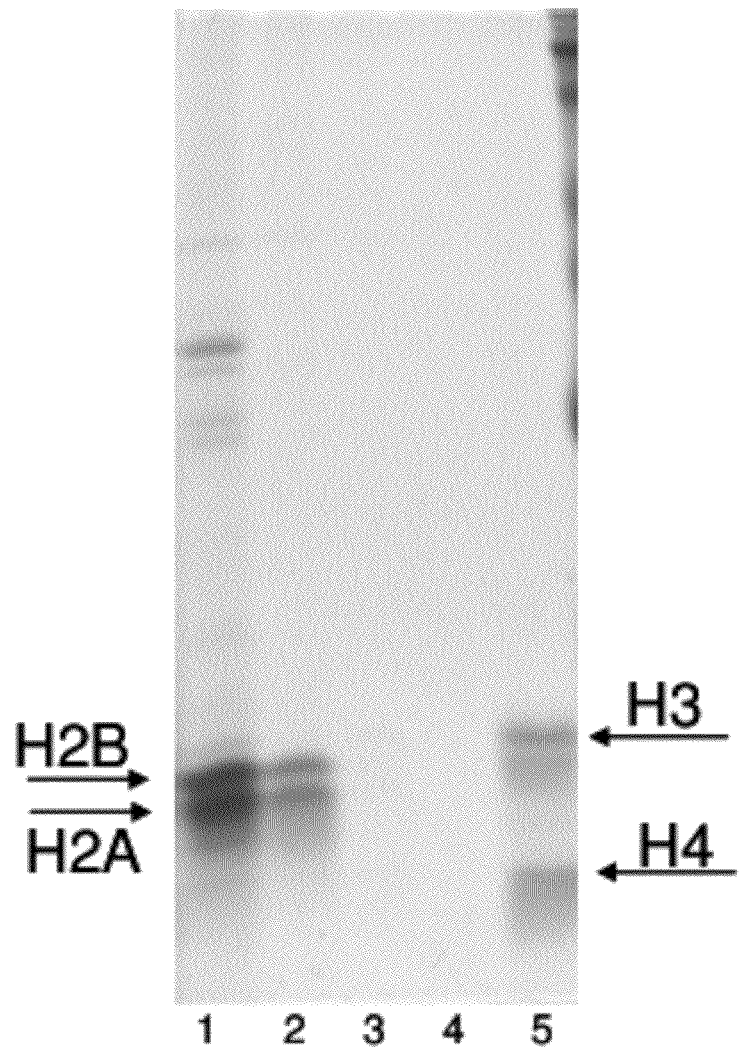
FIG. 10 is an SDS-PAGE of SP-purified H2B/H2A and H3/H4 from mitotically arrested and hypotonic-treated HeLa cells.

FIG. 10 is an SDS-PAGE of SP-purified H2B/H2A and H3/H4 from mitotically arrested and hypotonic-treated HeLa cells. Separation and recovery of H2A/H2B and H3/H4 from SP Sepharose were carried out as describe in the chromatographic protocol. H2A/H2B were eluted at 0.8 M NaCl; whereas, H3/H4 was recovered with 2 M NaCl. After separation, all fractions (1.5 mM each) were precipitated 20% TCA, overnight as described in the method. The histones were resuspended in 100 µl $H_2O$. 5 µl of proteins, from each step, were loaded as following. 1- and 2, 0.8 M NaCl-eluted H2A/B. 3-5, elution of H3/H4 in 2 M NaCl.

Figure 11:
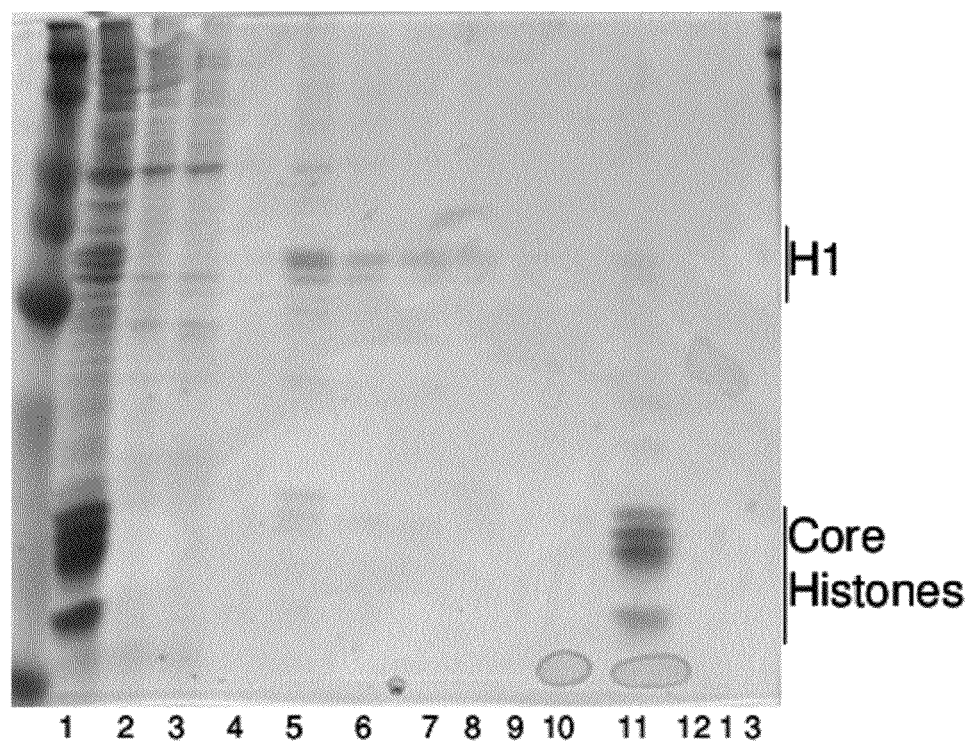
FIG. 11 is a gel showing SP Sepharose-purification of histones from hypotonically treated HeLa cells.

FIG. 11 is a gel showing SP Sepharose-purification of histones from hypotonically treated HeLa cells. Mitotic HeLa cells were incubated at room temperature in hypotonic buffer (10 mM Tris-HCl, pH 7, 40 mM NaCl (or KCl) for 20-30 min. Cell cytoplasm was lysed by adding 0.2% Triton/2 mM $MgCl_2$ and nuclei were extracted with 0.5 M NaCl. This treatment achieves maximum dephosphorylation of the histones that then can be used in control experiments (e.g. comparing the influence on chromatin dynamic of highly phosphorylated histones versus unphosphorylated one). The histones were extracted and purified as indicated in the SP-chromatographic method. The lanes are as follows: 1, 15 µl out 2.4 ml input protein to SP. 2, 20 µl out 2.4 ml of flow-through. 3, 20 µl out 1.5 ml wash with 0.5 M NaCl, 50 mM Tris-HCl, pH 8. 4-9, 20 μl out 1.5 ml wash with 0.6 M NaCl (H1 eluted at 0.6 M NaCl). 10-13, 10 μl of eluted core histones (1.5 ml fractions) at 2 M NaCl. Samples were diluted ¼ in 2× reducing sample buffer, implying that the protein loading for eluted core histones was 3.6-fold lower than for the input crude (lane 1).

As with all methods described herein, the above-described results for histone isolation are not limited to specific cell lines, cell cultured conditions (e.g. growing cell or mitotically arrested), particular tissues, or organs, etc. Thus, the methods for histone isolation are applicable to any biological specimens.

EXAMPLE 7

Isolation of H3 and H4 with
Pyridyl-thiopropyl-Sepharose [or
Activated-thiol-Sepharose (Pyridyl-gluthathion)

Figure 12:
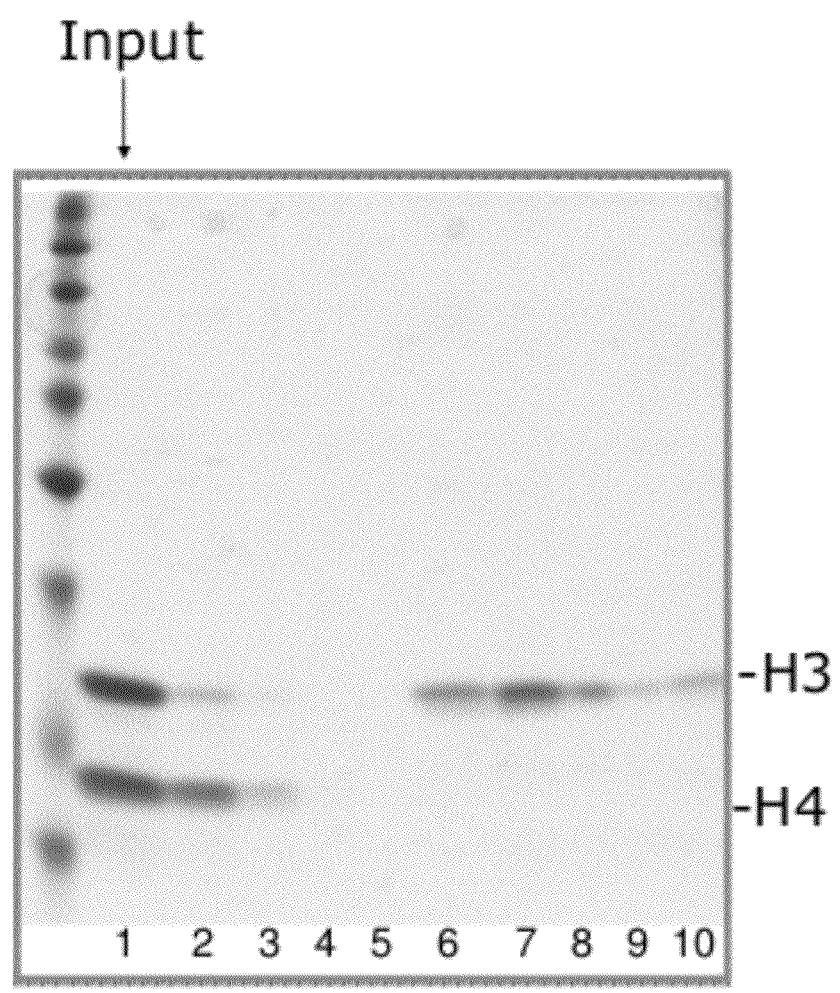
FIG. 12 shows histone preparations prepared from 1470.2 mouse breast carcinoma cells fractionated with pyridyl-thiopropyl-Sepharose.

Histone H3/H4 extracts from 1470.2 mouse breast carcinoma cells were incubated with pyridyl-thiopropyl-Sepharose [or activated-thiol-Sepharose (e.g., pyridyl-gluthation), data not shown; Sigma]. The input H3/H4 was derived either from salt-urea hydroxyapatite method or from sulfo-propyl Sepharose (SP) after stripping H1 (0.6 M) and H2A/H2B in 0.8 M NaCl, essentially as described above. Purified histone H3/H4 were eluted in 2 M NaCl, precipitated with 35% TCA, and resuspended in a denaturing solution comprising 8 M urea, 50 mM Tris-HCl, pH 8, 2 mM EDTA (EDTA serves to prevent Cys-SH oxidation). Then the urea solution of H3/H4 (0.4-0.2 mg/ml) was incubated with activated thiol (1:1, volume solution/volume swollen resin, pyridyl-thiopropyl-Sepharose (or activated-thiol-Sepharose (pyridyl-gluthation), data not shown; Sigma)) for 2.5 h at room temperature. A substitution reaction then occurs between the H3-exposed-SH groups and the immobilized pyridyl groups, where pyridyl is the leaving radical from immobilized thiopropyl-Sepharose (or activated glutathione Sepharose, data not shown). H4 mostly depleted of H3 (FIG. 12) lanes 2-4) was recovered in the matrix flow-through and washes. H3 was then eluted with 25-50 mM DTT, in the same urea buffer, at 37° C. with three-four changes every 30 min of fresh made DTT (FIG. 12, lanes 6-9; lane 10 is the resin treated under stronger stringency with 2× SDS-reducing sample buffer at 100° C. after DDT elution of H3 and serves as a control confirming the effectiveness of the DTT elution of H3 under mild conditions). Alternatively, activated thiol also serves to purify H3 from bulk histones mix (H1, H2AH2B/H4) eluted from SP (data not shown).

EXAMPLE 8

By using strong denaturing solutions, at onset and/or throughout the histone purification and fractionation processes, versatile, fast, and feasible methods were developed, yielding highly purified histone fractions, from intact cells, preserving their original covalent modifications. Contrasting reported methods, these methods bypass cell lysis, nuclei isolation and washes, and chromatin solubilization under mild conditions that can hinder histone native modifications and the integrity of histone's primary amino acid sequences. In addition, these methods bypass the need of a cumbersome technique such as HPLC for histone fractionation. The salt-urea-hydroxyapatite (SUHA) method yields highly purified H3/H4 from intact cells in one single step. The acidic-sulfo-propyl (SP) cation exchange method yields four independent homogeneous histone fractions: a) H1, b) purified whole core histones, c) isolated H2A/H2B, and d) fractionated H3/H4, from intact cells, in a single chromatographic step. Finally, the covalent-chromatography through activated-thio-propyl-Sepharose (ATS, or activated-thiol-Sepharose) method yields near 100% homogeneously isolated H3 and H4. The isolated histones are suitable for mass spectrometry analysis and basic experimental works such as nucleosome assembly. In addition, these procedures provide highly purified histones suitable for cancer diagnosis and in the prediction of cancer progression.

In additional detail, the overall rationale for the salt-urea-hydroxyapatite (SUHA) method is based on the concept that increasing salt concentration of aqueous solutions is believed to strengthen hydrophobic forces between interacting hydrophobic protein surfaces that are in turn resistant to be disrupted by high concentration of chaotropic agent such as urea (Catalysis in chemistry and enzymology, by William P. Jencks. Dover edition, 1987. Pages 358-436) or by low pH (2.5) glycine solution (Rodriguez, P., Fuentes, P., Munoz, E., Riveros, D., Orta, D., Alburqerque, S., Perez, S., Besada, V., and Herrera, L. (1994). The streptokinase domain responsible for plasminogen binding. *Fibrinolysis* 8, 276-285). Thus, we exploited this phenomenon to stabilize the macrostructure of nuclear envelop by salt solutions containing 8 M of urea; while solubilizing cell cytoplasm and extracting nuclear components others than H3/H4. Then, the stabilized nuclei containing chromatin-bound H3/H4 were recovered by microcentrifugation at 14K in high yield and purity.

Benefits

A macroscopic entity such as the nuclear envelop is stabilized in high urea concentration, for example, 8 M of urea by various salts, while the cellular cytoplasm and nuclear components are dissolved.

The stabilized nuclei and chromosomes can be readily isolated by microcentrifugation from the solubilized cytoplasm and nuclear components.

Natively modified (for example, hyperacetylated, methylated, ubiquityned, sumoylated, polyribosylated, phosphorylated, etc.), low-modified and unmodified H3/H4 and some H1 can be recovered, in high yield, and purity from the nuclear pellet.

H3/H4 and some H1 can be recovered in high yield and purity from the hydroxyapatite-chromatin complex.

This fractionation protects histone native co- and post-translational modifications, including nitrogen phosphorylations when the histones are recovered in neutral SDS-solutions.

Final histone extraction from the nuclear pellet or from hydroxyapatite-chromatin complex can be achieved by diluted strong acids.

Final histone extraction, from the nuclear pellet or from hydroxyapatite-chromatin complex can be achieved by neutral SDS solutions that would preserve histone nitrogen phosphorylations (e.g. histidine and lysine phosphorylations).

SDS extraction, specifically, protects histone nitrogen phosphorylations that would be destroyed by strong acids.

Isolated H3/H4 can be used in laboratory assays.

This method allows a direct determination of H3 and H4 masses by direct mass spectrometry techniques.

This method facilitates direct determination of H3 and H4 sequences.

This fractionation does not need complex, expensive and cumbersome techniques and instruments such as high performance liquid chromatography (HPLC).

The acidic-cation-exchange method (e.g., sulfopropyl-Sepharose, SP), solubilizes whole histones in sulfuric acid from intact and minimally perturbed cells. The SP method uses the unique feature of histones of having a strong positive charge to specifically adsorb them onto a conventional cation-exchange resin such as sulfopropyl-Sepharose, in high ionic strength buffer; while most contaminant proteins are dispensed in the flow-through. Then, the histones are fractionated by stepwise increments of NaCl concentration. This strategy yields three independent highly purified histone fractions: purified whole core histones; or isolated H2A/H2B and fractionated H3/H4, from intact cells in a single chromatographic step. Importantly, the SP method is able to purify and fractionate hyper-phosphorylated mitotic histones and hyper-acetylated core histones as well (data not shown).

Benefits

Solubilizes whole histones in sulfuric acid (or any strong diluted acid), from intact and minimally perturbed cells.

The histone acidic solubilization protects histones native modifications and primary sequences.

The histone acidic solubilization protect histones of being oxidized.

SP histone fractionation allows natively modified and unmodified whole core histone H2A/H2B/H3/H4 purification.

Whole core histones, natively modified and unmodified, can be used in laboratory assays.

Whole core histones can be used in diagnosis.

SP histone fractionation allows H1 isolation.

Isolated H1 can be used in laboratory assays.

This method allows a direct determination of H1 masses by direct mass spectrometry techniques.

H1 can be used in diagnosis.

This method allows a direct determination of H1 sequences.

SP histone fractionation allows H2A/H2B isolation.

Isolated H2A/H2B can be used in laboratory assays.

H2A/H2B can be used in diagnosis.

This method allows a direct determination of H2A and H2B masses by direct mass spectrometry techniques.

This method allows a direct determination of H2A and H2B sequences.

SP histone fractionation allows natively modified and unmodified H3/H4 isolation.

H3/H4 can be used in laboratory assays.

H3/H4 can be used in diagnosis.

This method allows a direct determination of H3 and H4 natively modified and unmodified masses by direct mass spectrometry techniques.

This method allows a direct determination of H3 and H4 sequences.

These fractionations do not need complex, expensive and cumbersome techniques and instruments such as high performance liquid chromatography (HPLC).

Finally, H3/H4 can be resolved by using the covalent-chromatography-method (thiopropyl-Sepharose-6B, TPS) (see e.g., Covalent chromatography. Preparation of fully active papain from dried papaya. Biochem J 133, 1973 573-584 for background), which specifically forms a reversible disulfur bond between the immobilized activated-thiopropyl-Sepharose beads and the reduced cysteine (Cys)-S—H group (s) on H3. Since H4 is devoid of Cys it is recovered in the TPS flow-through, while resin-bound-H3 is eluted at low concentration of reducing agents. This method yields near 100% homogeneously isolated H3 and H4. The fractionated histones are suitable for mass spectrometry analysis and basic experimental works such as nucleosome assembly.

Benefits

This method allows isolating natively modified and unmodified H3 from H4.

Isolated natively modified and unmodified H3 and H4 can be used in laboratory assays.

Isolated H3 and H4 can be used in diagnosis.

This method allows a direct determination of natively modified and unmodified H3 and H4 masses by direct mass spectrometry techniques.

This method allows a direct determination of H3 and H4 sequences.

This method allows isolating H3 from bulk histones (H1/H2A/H2B/H4) and from high mobility group proteins derived from SP method.

This method allows isolating H3 from bulk histones (H1/H2A/H2B/H4) and from high mobility group proteins, derived from SP method.

This method allows isolating H3 from bulk histones (H1/H2A/H2B/H4) and from high mobility group proteins obtained by other means.

H3 and H4 fractionation do not need complex, expensive and cumbersome techniques and instruments such as high performance liquid chromatography (HPLC).

Whereas, particular embodiments of the invention have been described above for purposes of description, it will be appreciated by those skilled in the art that numerous variations of the details may be made without departing from the invention as described in the appended claims.

We claim:

1. A method of isolating a chromatin fraction containing histone H1, H3 and H4 proteins from an intact cell comprising:
   a. lysing cells in a first solution comprising an enzyme-inhibitory concentration of a chaotropic reagent to produce a lysate comprising released chromatin, wherein either:
      i. the first solution comprises an ionic salt; or
      ii. an ionic salt is added to the lysate,
   wherein the ionic salt is included in the first solution or is added to the lysate in an amount effective, in the lysate, to prevent chromatin expansion and to facilitate dissociation, inactivation and extraction of cellular components other than H3, H4 and H1 from the chromatin;
   b. separating the released chromatin from cellular components other than H3, H4 and H1 histone proteins; and
   c. collecting the released chromatin.

2. The method of claim 1, wherein the ionic salt is fully ionic.

3. The method of claim 1, further comprising washing the released chromatin in a second solution comprising an enzyme-inhibitory concentration of a chaotropic reagent and an amount of an ionic salt effective to facilitate dissociation, inactivation and extraction of cellular components other than H3, H4 and H1 from the chromatin in the solution.

4. The method of claim 3, wherein the chaotropic reagent in one or both of the first and second solution is urea.

5. The method of claim 3, wherein one or both of the first and second solution comprises urea in a concentration of about 8 M or greater.

6. The method of claim 3, further comprising extracting H3 and H4 histone proteins from the released chromatin.

7. The method of claim 6, further comprising separating the H3 histone protein from the H4 histone protein.

8. The method of claim 7, wherein the H3 histone protein and the H4 histone protein are separated by affinity chromatography using one or both of an anti-H3 histone binding reagent or anti-H4 histone binding reagent.

9. The method of claim 7, wherein the H3 histone protein and the H4 histone protein are separated by attaching the H3 histone protein to a sulfhydryl-reactive group attached to a surface and washing H4 histone protein from the surface.

10. The method of claim 9, wherein the sulfhydryl-reactive group is chosen from one or more of maleimide; haloacetyl; pyridyl disulfide; pyridyl-thiopropyl; pyridyl-glutathion; N-succinimidyl-6-(3'-(2-pyridyldithio)-propionamido)-hexanoate; N-succinimidyl-3-(2-pyridyldithio)-propionate; sulfosuccinimidyl-6-(3'-(2-pyridyldithio)-propionamido)-hexanoate); activated thiol; thiopropyl; 3-(2-pyridyldithio) propionyl hydrazide; 4-succinimidyloxycarbonyl-methyl-a-[2-pyridyldithio]toluene; and 1-methylpropyl 2-imidazoylyl disulfide.

11. The method of claim 9, wherein the sulfhydryl-reactive group is one or both of pyridyl-thiopropyl and pyridyl-gluthation.

12. The method of claim 9, wherein the surface is a bead.

13. The method of claim 12, wherein the bead comprises agarose.

14. The method of claim 9, wherein the H3 histone protein is attached to the surface by a disulfide bond.

15. The method of claim 14, wherein the H3 histone protein is eluted from the surface with a solution comprising a reducing agent capable of breaking the disulfide bond.

16. The method of claim 15, wherein the solution comprising a reducing agent comprises one or more off β-mercaptoethanol, dithiothreitol and Tris(2-carboxyethyl)phosphine).

17. The method of claim 6, wherein the H3 and H4 histone proteins are acid-extracted from the DNA.

18. The method of claim 17, wherein the acid is $H_2SO_4$.

19. The method of claim 6, wherein the extracted H3 and H4 histone proteins are precipitated in one or more of perchloric acid and trichloroacetic acid.

20. The method of claim 19, wherein the proteins are precipitated in trichloroacetic acid.

21. The method of claim 19, wherein the proteins are precipitated in perchloric acid, thereby retaining residual H1 histone protein in the supernatant.

22. The method of claim 21, wherein the acid is about 5% perchloric acid.

23. The method of claim 6, further comprising determining if one or both of the H3 and H4 histone proteins are able to supercoil relaxed DNA.

24. The method of claim 3, wherein the first and second solution are the same.

25. The method of claim 3, wherein the chromatin is washed on a filter membrane.

26. The method of claim 25, wherein the filter membrane is contained within a centrifuge filter.

27. The method of claim 1, comprising centrifuging the cell lysate to produce a chromatin pellet and a supernatant and aspirating the supernatant.

28. The method of claim 1, wherein the chaotropic reagent is one of urea, thiourea, guanidium isothiocyanate, guanidium HCl or LiI.

29. The method of claim 1, wherein the salt comprises one or more of the following ions: Mg, Ca, Na, K, Li, $NH_4$, $SO_4$, acetate, Cl, F, Br, I, phosphate, bicarbonate and borate.

30. The method of claim 1, wherein the salt is NaCl.

31. The method of claim 30, wherein the lysis solution comprises from about 1 mM to about 1M NaCl.

32. The method of claim 30, wherein the lysis solution comprises from about 10 mM to about 800 mM NaCl.

33. The method of claim 30, wherein the lysis solution comprises from about 10 mM to about 200 mM NaCl.

34. The method of claim 30, wherein the lysis solution comprises from about 200 mM to about 400 mM NaCl.

35. The method of claim 1, comprising adsorbing the lysate to a non-sequence-specific DNA adsorbing material.

36. The method of claim 35, wherein the non-sequence-specific DNA adsorbing material is a calcium phosphate.

37. The method of claim 35, wherein the non-sequence-specific DNA adsorbing material is hydroxyapatite.

38. The method of claim 1, wherein an amount of the ionic salt effective to prevent chromatin expansion in the lysate is added to the lysate.

39. The method of claim 38, wherein a non-sequence-specific DNA adsorbing material is added to the lysate after the salt is added.

40. The method of claim 39, wherein the non-sequence-specific DNA adsorbing material is a calcium phosphate.

41. The method of claim 39, wherein the non-sequence-specific DNA adsorbing material is hydroxyapatite.

42. The method of claim 39, further comprising acid-eluting histone proteins from the non-sequence-specific DNA adsorbing material.

43. The method of claim 42, further comprising precipitating H3 and H4 histone proteins from the eluted histone proteins with perchloric acid.

44. The method of claim 43, comprising separating the H3 histone protein from the H4 histone protein.

45. The method of claim 1, wherein the cells are obtained from a tissue sample.

46. The method of claim 45, wherein the tissue sample is homogenized.

47. The method of claim 46, wherein the tissue sample is homogenized in the first solution.

48. A method of evaluating chromatin structure or histone modification patterns comprising, evaluating one or more of post-translational modification patterns, DNA binding patterns and chromatin assembly function of a chromatin fraction prepared according to the method of claim 1.

49. The method of claim 48, wherein the chromatin fraction is selected from the group consisting of:
  a) chromatin containing predominantly H1, H3 and H4 histone proteins;
  b) a mixture of H1, H3 and H4 histone proteins;
  c) a mixture of isolated H3 and H4 histone proteins; and
  d) isolated H1, H3 or H4 histone proteins.

50. The method of claim 48, wherein the chromatin fraction is evaluated for one or more of the following post-translational modifications: phosphorylation, acetylation, methylation, ubiquitination, sumoylation, poly-ribosylation, poly-polyglutamylation, nitrosylation and sulfatation.

51. The method of claim 48, wherein the chromatin fraction is evaluated for chromatin assembly function by determining the ability of proteins of the chromatin fraction to supercoil DNA in a DNA supercoiling assay.

52. A method of separating histone H3 protein from histone H4 protein in a sample comprising histone H3 and H4 proteins comprising binding histone H3 protein to a sulfhydryl-reactive group attached to a surface and washing histone H4 from the surface, wherein the sulfhydryl-reactive group is selected from the group consisting of maleimide; haloacetyl; pyridyl disulfide; pyridyl-thiopropyl; pyridyl-glutathion; N-succinimidyl-6-(3'-(2-pyridyldithio)-propionamido)-hexanoate; N-succinimidyl-3-(2-pyridyldithio)-propionate; sulfosuccinimidyl-6-(3'-(2-pyridyldithio)-propionamido)-hexanoate); activated thiol; thiopropy; 3-(2-pyridyldithio) propionyl hydrazide; 4-succinimidyloxycarbonyl-methyl-a-[2-pyridyldithio]toluene; and 1-methylpropyl 2-imidazoylyl disulfide.

53. The method of claim 52, further comprising eluting histone H3 from the surface with a reducing agent after washing histone H4 from the surface.

54. The method of claim 52, wherein the surface is a bead.

55. The method of claim 52, wherein the sulfhydryl-reactive group is one or both of pyridyl-thiopropyl and pyridyl-gluthation.

56. The method of claim 52, wherein the surface is an agarose bead.

57. A method of isolating histone proteins from cells comprising extracting the cells in an acid to produce an extract, neutralizing the acid, binding the extract to a cationic exchange material at a salt concentration at which histone proteins bind to the cationic exchange material, eluting one or more histone proteins with an elution solution having a salt concentration sufficiently high to elute the one or more histone proteins.

58. The method of claim 57, in which the cationic exchange material is a cationic exchange resin.

59. The method of claim 57, in which the cationic exchange material is sulfopropyl agarose.

60. The method of claim 57, wherein the salt is NaCl.

61. The method of claim 57, in which the extract is bound to the cationic exchange material in NaCl in a concentration of less than 0.5 M.

62. The method of claim 57, further comprising between the binding step and the eluting step washing the cationic exchange material.

63. The method of claim 62, wherein the cationic exchange material is washed with 0.5 M or less NaCl.

64. The method of claim 57, comprising eluting histone H1 protein with an elution solution having a salt concentration effective to elute histone H1 protein, but essentially not other histone proteins.

65. The method of claim 64, in which the histone H1 protein is eluted in 0.6 M NaCl.

66. The method of claim 57, comprising eluting core histone proteins from the cationic exchange material with an elution solution having a salt concentration effective to elute the core histones from the cationic exchange material.

67. The method of claim 57, comprising eluting histone H2A and H2B proteins with a first elution solution having a salt concentration effective to elute histone H2A and H2B proteins, but essentially not histone H3 or H4 histone proteins.

68. The method of claim 67, in which the first elution solution comprises NaCl in a concentration ranging from 0.7 M to less than 1 M.

69. The method of claim 67, in which the first elution solution comprises 0.8 M NaCl.

70. The method of claim 67, further comprising after eluting the histone H2A and H2B proteins, eluting histone H3 and H4 proteins with a second elution solution having a salt concentration effective to elute histone H3 and H4 proteins.

71. The method of claim 70, in which the second elution solution comprises NaCl in a concentration greater than 1M.

72. The method of claim 57, in which the acid is $H_2SO_4$.

73. The method of claim 72, in which the cells are extracted in 0.1M to 0.25 M $H_2SO_4$.

74. The method of claim 27, further comprising placing the chromatin pellet on a filter membrane and washing the chromatin pellet.

* * * * *

UNITED STATES PATENT AND TRADEMARK OFFICE
CERTIFICATE OF CORRECTION

PATENT NO. : 8,163,481 B2  
APPLICATION NO. : 12/061234  
DATED : April 24, 2012  
INVENTOR(S) : Pedro Rodriguez-Collazo et al.

Page 1 of 1

It is certified that error appears in the above-identified patent and that said Letters Patent is hereby corrected as shown below:

Title page, Item (73) Assignees, Line 2, delete "Systems" and insert -- System --

Column 27, Line 28, Claim 16, delete "off" and insert -- of --

Column 27, Line 13, Claim 10, delete "imidazoylyl" and insert -- imidazolyl --

Column 27, Line 17, Claim 11, delete "gluthation" and insert -- glutathion --

Column 27, Line 29, Claim 16, delete "phosphine)." and insert -- phosphine. --

Column 28, Line 64, Claim 52, delete "thiopropy;" and insert -- thiopropyl; --

Column 28, Line 66, Claim 52, delete "imidazoylyl" and insert -- imidazolyl --

Column 29, Line 7, Claim 55, delete "gluthation" and insert -- glutathion --

Signed and Sealed this  
Eleventh Day of September, 2012

David J. Kappos  
*Director of the United States Patent and Trademark Office*